(12) United States Patent
Uenishi et al.

(10) Patent No.: US 7,078,687 B2
(45) Date of Patent: Jul. 18, 2006

(54) THIN FILM ANALYZING METHOD

(75) Inventors: Kazuya Uenishi, Shizuoka-ken (JP); Kazuyuki Kitada, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 54 days.

(21) Appl. No.: 10/756,753

(22) Filed: Jan. 14, 2004

(65) Prior Publication Data
US 2004/0232330 A1 Nov. 25, 2004

(30) Foreign Application Priority Data
Jan. 15, 2003 (JP) .............................. 2003-007362

(51) Int. Cl.
*G21K 7/00* (2006.01)
*H01J 37/305* (2006.01)

(52) U.S. Cl. .................... 250/306; 250/307; 250/310; 250/309

(58) Field of Classification Search ................ 250/306, 250/307, 309, 310, 316.1, 318; 430/270.1, 430/293, 270.11, 286.1, 300, 301; 117/95, 117/101
See application file for complete search history.

(56) References Cited

U.S. PATENT DOCUMENTS

| 4,153,330 | A | * | 5/1979 | Tomlinson, III ............. 385/35 |
| 4,858,556 | A | * | 8/1989 | Siebert ....................... 118/664 |
| 4,950,548 | A | * | 8/1990 | Furusawa et al. ........... 428/611 |
| 5,270,552 | A | * | 12/1993 | Ohnishi et al. ............. 250/307 |
| 5,410,172 | A | * | 4/1995 | Koizumi et al. ............. 257/347 |
| 5,411,631 | A | * | 5/1995 | Hori et al. ..................... 216/72 |
| 5,462,762 | A | * | 10/1995 | Onuma et al. ................ 427/63 |
| 5,610,392 | A | * | 3/1997 | Nagayama et al. ......... 250/226 |
| 5,637,445 | A | * | 6/1997 | Machida et al. ............ 430/533 |
| 5,645,909 | A | * | 7/1997 | Kobayashi et al. ........ 428/64.1 |
| 5,665,980 | A | * | 9/1997 | Onuma et al. ................ 257/35 |
| 5,842,387 | A | * | 12/1998 | Marcus et al. ............. 76/104.1 |
| 6,008,491 | A | * | 12/1999 | Smentkowski et al. ..... 250/309 |

(Continued)

FOREIGN PATENT DOCUMENTS

JP 7-285275 A 10/1995

OTHER PUBLICATIONS

"63th Applied Physics Scientific Lecture Meeting Proceedings," Man et al, Lecture No. 27a-Q-5 (2002).

*Primary Examiner*—John R. Lee
*Assistant Examiner*—Bernard E. Souw
(74) *Attorney, Agent, or Firm*—Sughrue Mion, PLLC

(57) ABSTRACT

The present invention provides is a thin film analyzing method which can be applied to various fields, and which makes it possible to detect and analyze in a simple manner, with high precision, a distribution of a specific component in a thin film formed on a support. The method for analyzing a constituent of a thin film comprises a cutting step of cutting the thin film obliquely, and an analyzing step of analyzing a specific component in the cut section of the thin film. In this cutting step, the thin film is preferably cut with a microtome to which a cutting edge made of glass is fitted knife made of glass. The analysis of the distribution of the specific component in the cut section is suitably analyzed by TOF-SIMS or $\mu$-ESCA. The method is particularly useful for analyzing an image recording layer of a planographic printing plate precursor which comprises a water-insoluble and alkali-soluble resin, an infrared ray absorber, and a colorant.

26 Claims, 3 Drawing Sheets

U.S. PATENT DOCUMENTS

| | | |
|---|---|---|
| 6,054,333 A * | 4/2000 | Bensaoula ................ 438/9 |
| 6,214,107 B1 * | 4/2001 | Kitabatake ................ 117/95 |
| 6,270,573 B1 * | 8/2001 | Kitabatake et al. ......... 117/95 |
| 6,273,950 B1 * | 8/2001 | Kitabatake ................ 117/95 |
| 6,534,240 B1 * | 3/2003 | Hoshi ..................... 430/302 |
| 6,614,532 B1 * | 9/2003 | Power et al. ............. 356/432 |
| 6,791,320 B1 * | 9/2004 | Hasegawa et al. ......... 324/252 |
| 6,830,863 B1 * | 12/2004 | Wachi et al. ............ 430/200 |
| 6,914,244 B1 * | 7/2005 | Alani ..................... 250/307 |
| 2004/0217286 A1 * | 11/2004 | Alani ..................... 250/304 |
| 2004/0232330 A1 * | 11/2004 | Uenishi et al. ........... 250/306 |

* cited by examiner

THIN FILM ANALYZING METHOD

CROSS-REFERENCE TO RELATED APPLICATION

This application claims priority under 35 USC 119 from Japanese Patent Application No.2003-7362, the disclosure of which is incorporated by reference herein.

BACKGROUND OF THE INVENTION

1. Field of the Invention

The present invention relates to a thin film analyzing method useful for analyzing a specific component contained in a thin film comprising various components. More specifically, the invention relates to a thin film analyzing method useful for analyzing an effective component contained in an image recording layer of a planographic printing plate precursor, and which is capable of measuring, with high precision, the type, content, distribution and other factors of a component contained in the layer.

2. Description of the Related Art

Recent development in laser technology has progressed rapidly. In particular, solid lasers and semiconductor lasers having emission wavelengths within the range from near infrared ray wavelengths to infrared ray wavelengths, with both high-power and small size are readily available. These lasers are very useful for exposure light sources for recording materials, such as a planographic printing plate precursor, which is made from digital data in a computer or the like.

The recording material used in the recording layer of a positive planographic printing plate precursor for infrared ray lasers is a composition comprising, as essential components, a binder resin soluble in aqueous alkali solution, an infrared ray absorber (hereinafter referred to as "IR dye" as the case may be), which absorbs light to generate heat, and other components. When a coating, that is, a recording layer is formed on a support, the IR dye or the like in the recording layer interacts with the binder resin in a non-exposed portion (image portion), so as to function as a dissolution inhibitor for substantially lowering the solubility of the binder resin. Thus, the coating having resistance against development is maintained. In contrast, in an exposed portion (non-image portion), the interaction between the IR dye or the like and the binder resin is made weak by generated heat, so that the solubility of the binder resin in alkali developing solution is improved. Thus, after developing treatment, the non-image portion is removed and the maintained image portion is imagewise distributed. In this way, a planographic printing plate is formed.

However, in such a positive planographic printing plate material for development by infrared ray lasers, a difference between the resistance against solubility of the non-exposed portion (image portion) and the solubility of the exposed portion (non-image portion) is in-sufficient under various usage conditions. Thus, dependending on a variation in usage conditions, the following problems are easily caused: excessive development, that is, a film-decreasing phenomenon, which is generated by the dissolution of the coating in the image portion with the developing solution; poor development, that is, a film-remaining phenomenon, which is caused by failure of coating to be sufficiently dissolved and removed with the developing solution in the non-image portion; and other problems. In the case that a user's finger contacts the surface of the recording layer at the time of handling the plate material, thereby changing the surface state slightly, the non-exposed portion (image portion) is dissolved from the changed portion as a starting point at the time of developing the plate material. As a result, a scar state is generated so as to cause problems that the printing resistance deteriorates and the inking property becomes poor.

Such problems result from essential differences in plate-making mechanisms between positive planographic printing plate materials for infrared ray lasers and positive planographic printing plate materials made by UV exposure. In other words, positive planographic printing plate material made by UV exposure comprises, as essential components, a binder resin soluble in aqueous alkali solution, and an onium salt or quinone diazide compound. However, the onium salt or quinone diazide compound interacts with the binder resin in the non-exposed portion (image portion), to function as a dissolution inhibitor, and further in the exposed portion (non-image portion) the salt or compound is decomposed by light and gives an acid to function as a dissolution promoter. That is, the salt or compound has two functions.

In contrast, the IR dye or the like in the positive planographic printing plate material for infrared ray lasers functions only as a dissolution inhibitor for the non-image portion (image portion), and does not promote dissolution of the exposed portion (non-image portion). Therefore, in order to make the difference between the solubility of the non-exposed portion and that of the exposed portion evident in the positive planographic printing plate material for infrared ray lasers, it is necessary to use, as the binder resin therein, a resin having a high solubility in alkali developing solution. However, when such a binder resin is used, a problem of an unstable state before development is caused. If a binder resin having a low solubility in alkali developing solution is used to improve the strength of the image portion, the sensitivity is liable to be lowered or the film is liable to remain. Thus, the following serious problem is caused: the scope of developing-conditions for keeping the difference between the solubility of the image portion and that of the non-image portion (hereinafter referred to as development latitude) becomes narrow.

Various techniques have been developed to make the development latitude wide. For example, there is known a positive photosensitive image forming material comprising a resin which has a phenolic hydroxyl group and is soluble in aqueous alkali solution (for example, novolak resin), a substance which absorbs light to generate heat, and a positive photosensitive compound (for example, any one of various onium salts and quinine azide compounds) (see, for example, Japanese Patent Application Laid-Open (JP-A) No. 7-285275). In such an image forming material, the positive photosensitive compound functions as a dissolution inhibitor for substantially lowing the solubility of the aqueous alkali solution soluble resin in the image portion, and in the non-image portion this compound does not exhibit dissolution inhibiting capability caused by heat, so that the compound is removed by development. As a result, an image is formed. In the case of such a positive image forming material, electrostatic interaction between the alkali soluble resin and the dissolution inhibitor is cancelled by heat generated from exposure, thereby improving the alkali solubility and removing the exposed portion by development, so as to form an image. This image forming material is characterized by using a thermally reversible reaction and small structural change of the material. Thus, it is feared that a sufficient dissolution promoting effect cannot be obtained and conversely various performances, such as processing stability and development latitude, are affected.

As described above, in the development of methods for providing preferable properties to planographic printing plate precursors, there are limitations in only investigating the mean for selecting components in the composition used in the image forming layer of the precursors. It has become necessary to investigate the physical properties of the inside of the image recording layer.

The present Applicant investigated this issue and then suggested a planographic printing plate precursor characterized in that the distribution of an infrared ray absorber and that of a colorant are different from each other in an image recording layer in order to improve the development latitude thereof. In such a case, it is important to accurately analyze correctly how the respective materials are distributed in the image recording layer which is a thin film.

Hitherto, various methods have been adopted in order to analyze the distribution of a material in a thin film along the depth direction thereof. For example, the step of using an ion gun or the like to sputter high energy beams to a coating and then subjecting the surface thereof to elementary analysis by X-ray photoelectron spectroscopy is repeated to analyze components, in the thin coating surface, which are not removed by the sputtering, whereby information about the thin coating along the depth direction thereof can be obtained. In this case, however, there is a high risk that materials in the thin coating are destroyed by the irradiation with the high energy beams from the ion gun or the like used in the sputtering. Thus, precise information cannot be easily obtained. In particular, when an organic compound present in the thin coating is detected, the compound is decomposed or evaporated by the irradiation with the high energy beams. Thus, precise measurement cannot be attained.

In recent years, a method has been suggested which comprises the steps of using a device called SAICAS (manufactured by DAIPLA WINTES Co., Ltd.) to cut a coating obliquely and then analyzing information along the depth direction by TOF-SIMS (see, for example, "63th, Applied Physics Scientific Lecture Meeting Proceedings" Lecture No. 27a-Q-5 (2002)). However, this device is originally a device for measuring exfoliating strength or shear strength. When this device is used to cut a coating obliquely to form an enlarged cross section, the following problems occur: (1) material of the cutting edge (knife) of the device is expensive diamond, and the cutting edge surface gets dirty with repeated usage of the cutting edge; (2) the cutting speed is very low (0.1 to 100 μm/sec), so that a long time is required for forming a sample; (3) when the device is applied to a planographic printing plate precursor, the tip of the cutting edge is damaged, which is minutely worked, because of high hardness of the support of the plate precursor, and the device is unsuitable for cutting the plate precursor from the surface of the coating to the support; and (4) the cut section is wavy and a flat and smooth cut face cannot be obtained.

As described above, many problems arise in analyzing a thin coating, particularly in analyzing information on a coating formed on a support along the depth direction thereof. Under the present circumstances, satisfactory results cannot be obtained according to conventional methods.

SUMMARY OF THE INVENTION

An object of the present invention is to provide a thin film analyzing method which can be applied to various fields, and which makes it possible to detect and analyze in a simple manner, with high precision, the presence and absence and the distribution of a thin film, particularly a specific component in a thin film formed on a support. Another object of the invention is to provide a thin film analyzing method particularly useful for detecting the distribution of a substance in an image recording layer of a planographic printing plate precursor.

The inventors carried out earnest investigation, and as a result discovered that by using a method to be described below, the objects of the invention can be attained, and have made the invention.

That is, the thin film analyzing method of the invention is a method for analyzing a constituent of a thin film, which comprises a cutting step of cutting the thin film obliquely and an analyzing step of analyzing the cut section of the thin film.

The thin film to be analyzed may be a thin film formed on a support. The thin film to be analyzed may be a monolayered thin film or a thin film having a multilayered structure. Among the plural layers in the multilayered structure, only one layer may be analyzed or two or more layers may be analyzed.

A preferable aspect of the analyzing step in the method of the invention is a step of measuring the distribution state of a specific component in a cut section of a thin film. In this analyzing step, the distribution state of the specific component is preferably analyzed by TOF-SIMS (Time-Of-Flight Secondary Ion Mass Spectrometry) or μ-ESCA (X-ray Electron Spectroscopy for Chemical Analysis) from the viewpoint of precision.

In the cutting step, the thin film is preferably cut with a microtome to which a cutting edge made of glass is fitted.

This analyzing method can be suitably applied to the image recording layer of a planographic printing plate precursor, which is a thin film comprising a water-insoluble and alkali-soluble resin, an infrared ray absorber, and a colorant.

The following describes preferable aspects of the thin film analyzing method of the invention.

(1) An aspect in which a direction of the cutting is made to a direction from the surface of the thin film to a support on which the thin film is formed in the cutting step.

(2) An aspect in which an angle for the cutting is set to 5° or less in the cutting step, thereby enlarging the cut section 10 to 2800 times in a film thickness direction as compared with a case in which the thin film is cut perpendicularly to the surface of the thin film, and then measuring the distribution state of a specific component in the coating.

(3) An aspect in which an edge angle of a cutting edge used for the cutting is 55° or less in the cutting step.

(4) An aspect in which a microtome is used for the cutting in the cutting step.

(5) An aspect in which the cutting speed is 0.1 mm/second or more in the cutting step.

(6) An aspect in which the film thickness of the thin film to which the method of the invention is applied is from 0.05 to 3 μm.

(7) An aspect in which the thin film to which the method of the invention is applied is formed on a support, the support being an Al substrate or an Si substrate.

(8) An aspect in which the thin film to which the method of the invention is applied is a photosensitive coating. When the thin film is photosensitive, the distribution state of a specific component in the thin film can be analyzed before and after exposure to light.

The thin film analyzing method of the invention can be applied to various fields, and makes it possible to detect and analyze in a simple manner, with high precision, the distribution of a specific component in a thin film formed on a support. The thin film analyzing method of the invention is particularly useful for detecting the distribution of a substance in the image recording layer of a planographic printing plate precursor.

DETAILED DESCRIPTION OF THE INVENTION

The present invention is described in detail, hereinafter.

A thin film analyzing method of the invention comprises (1) a cutting step of cutting a thin film obliquely, and (2) an analyzing step of analyzing the cut section of the thin film.

These steps are successively described hereinafter.

(1) Cutting Step of Cutting a Thin Film Obliquely.

A direction along which a thin film is cut can be selected at will. A thin film formed on a support is preferably cut from the surface of the thin film toward the support. By cutting the thin film in this direction, the cutting is completed at the same time as when the cutting means reaches the support, and therefore the cut face is not affected even if the cutting means is damaged by the support. For this reason, a flat and smooth cut face (analyzing face) with no waves can be obtained.

The cutting means can be selected at will from known means. As described above, it is unpreferable to use a knife the material of which is expensive diamond for the following reasons: when the edge of the knife is exchanged for each sample, costs increase because of the exchange; and when the edge is used without being exchanged, components of the thin film adhere to the surface of the edge, and if in this state the next sample is cut, it is feared that the cut face is contaminated by the components adhering to the surface of the edge and the precision in measurement may fall.

As the cutting means, a known microtome can be used. The microtome is a conventional device used for cutting thinly an object to be observed with a microscope and preparing a sample thereof. The microtome is usually used to slice an object thinly and horizontally. In the method of the invention, this microtome is used to cut the object obliquely without slicing the object thinly and horizontally. It was discovered in the invention that a preferable cut face can be obtained by selecting the edge angle and the material of a knife and cutting a thin film obliquely in accordance with a method which is entirely different from conventional methods.

Figure 1A:
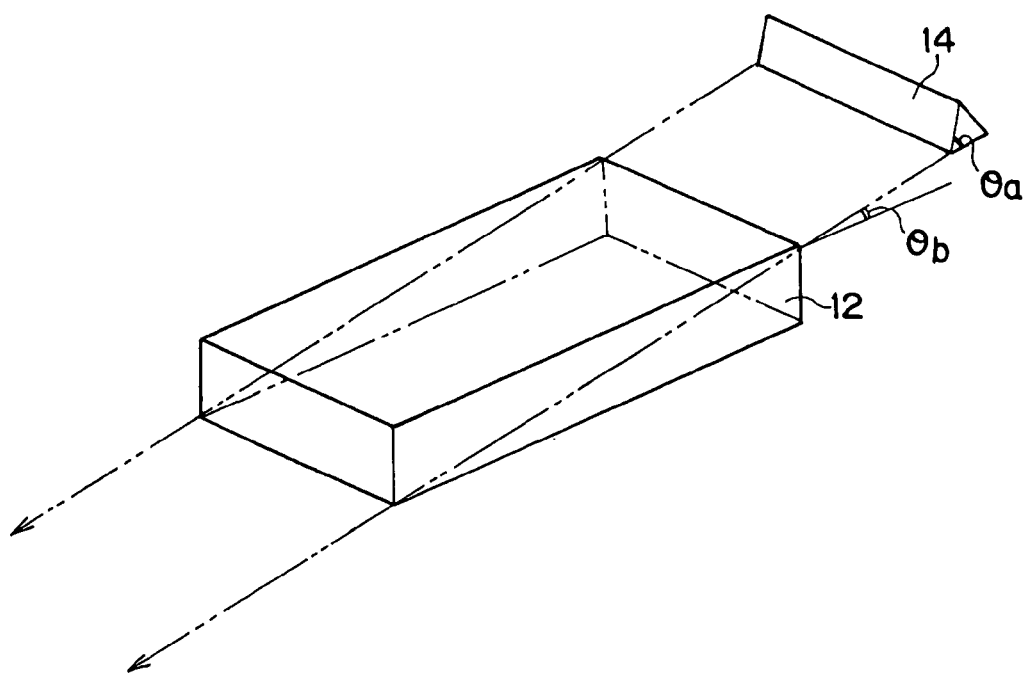
FIG. 1A is a perspective view which schematically illustrates a state in which a thin film is cut with a cutting edge of a microtome.
Figure 1B:
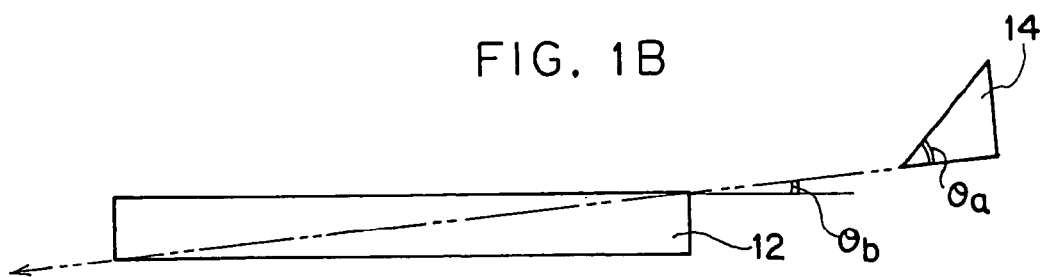
FIG. 1B is a schematic sectional view thereof.

The following describes preferable embodiments in which a microtome is used as the cutting means, and advantageous effects thereof. FIG. 1A is a perspective view which schematically illustrates a state in which a thin film 12 is cut with a cutting edge 14 of a microtome, and FIG. 1B is a schematic sectional view thereof. The direction along which the thin film is cut is shown by arrows.

Figure 2A:
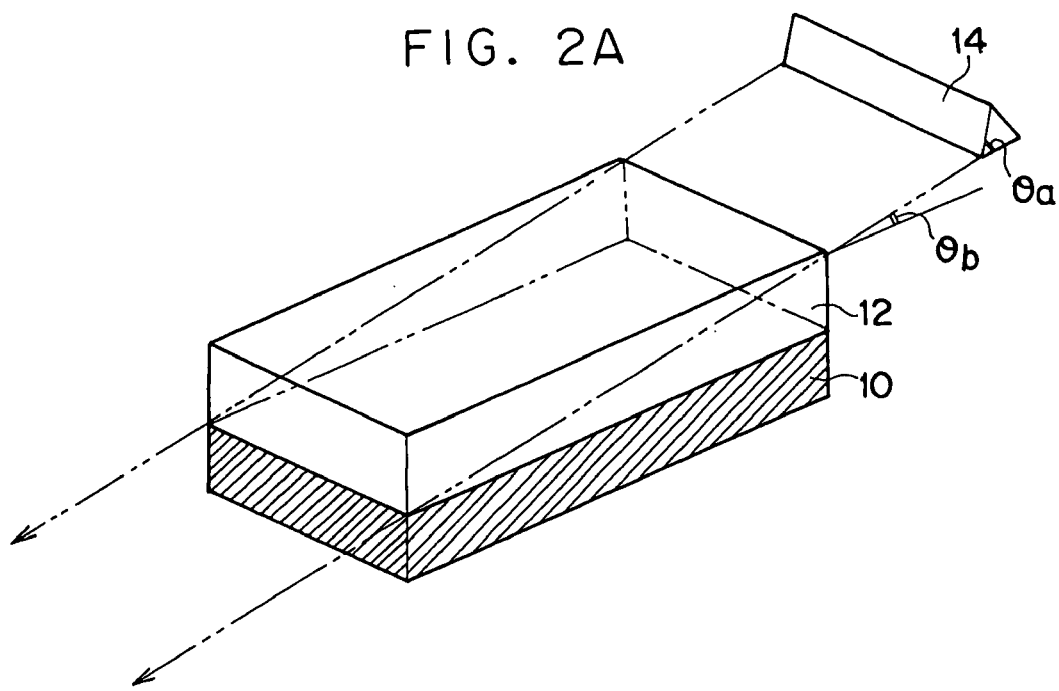
FIG. 2A is a perspective view which schematically illustrates a state in which a thin film formed on a support is cut with a cutting edge of a microtome.
Figure 2B:
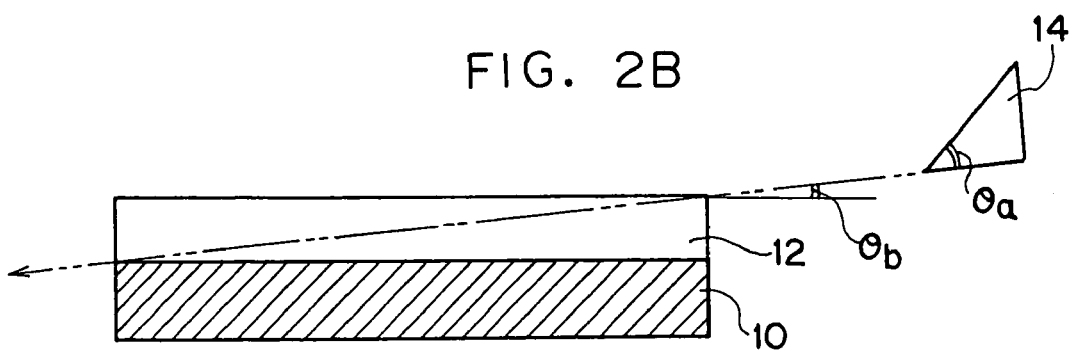
FIG. 2B is a schematic sectional view thereof.

FIG. 2A is a perspective view which schematically illustrates a state in which a thin film 12 formed on a support 10 is cut with a cutting edge 14 of a microtome, and FIG. 2B is a schematic sectional view thereof.

As the cutting edge 14 of the microtome, an inexpensive glass knife is preferably used. In this way, each sample can be cut with a new glass knife without incurring high costs. By exchanging the glass knife in this way, it is possible to control contamination of the cut face caused by the knife.

The cutting edge (glass knife) 14 can be easily processed, and the edge angle thereof can be set to any angle. By setting the edge angle $\theta a$ (see FIG. 1) of the cutting edge into an angle as sharp as 55° or less, a flat and smooth cut section can be obtained. When the knife having such a sharp angle is used to cut the thin film 12, an advantage is that the smoothness of the cut face is remarkably improved as compared with cutting (edge angle: 60°) according to the SAICAS method, which is generally used. The edge angle $\theta a$ of the cutting edge is more preferably from 25 to 50°. If a cutting edge having an edge angle $\theta a$ of more than 55° is used to cut the thin film 12, it is feared that a flat and smooth cut face cannot be obtained.

When the microtome is used to cut the thin film 12, the film can be cut at a speed as high as 0.1 mm/second or more. Thus, the cutting step can be performed rapidly carried out. As a result, the invention has an advantage in that a sample used in the analyzing step can be prepared rapidly.

As illustrated in FIG. 2A and FIG. 2B, by controlling the cutting angle and size of a sample, the cutting of the thin film 12 from the surface of the film 12 to a support 10 can be adjusted so as not to bring the edge point of the cutting edge 14 into contact with the support 10.

According to any microtome, cutting angle $\theta b$ (see FIG. 1A and FIG. 1B) can be adjusted to 5 to 0.02°. In this case, the section of the thin film can be made 10 to 3000 times larger than the section in the case of cutting the thin film perpendicularly. The cutting angel $\theta b$ is preferably 1° or less, and more preferably 0.5° or less. In this way, the cut section is enlarged 100 times or more, which is preferable from the viewpoint of highly precise analysis.

Figure 3A:
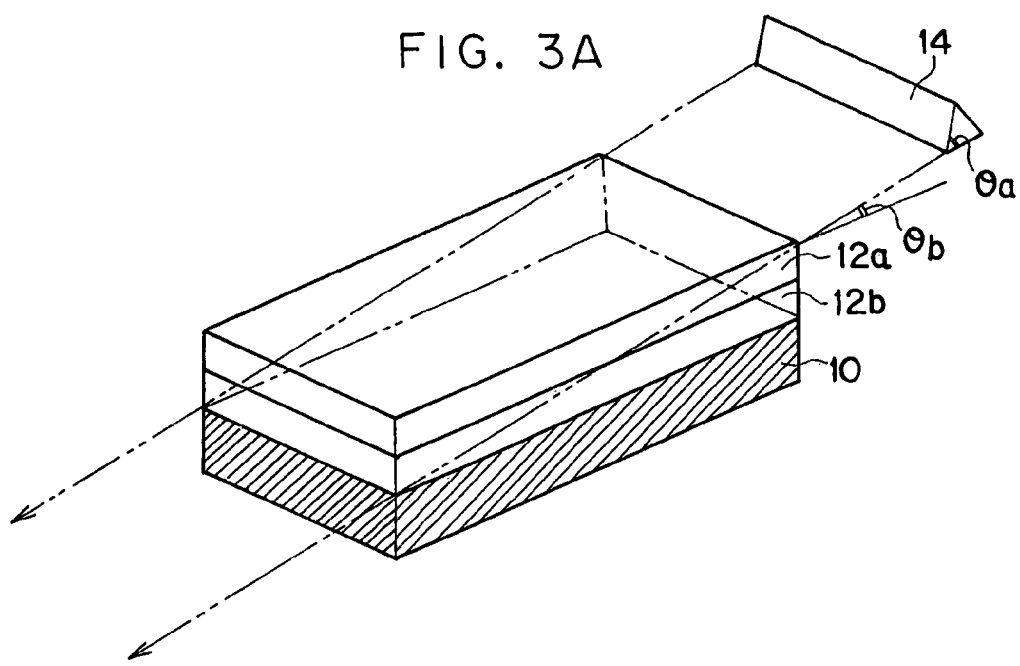
FIG. 3A is a perspective view which schematically illustrates a state in which a multilayered thin film formed on a support is cut with a cutting edge of a microtome.
Figure 3B:
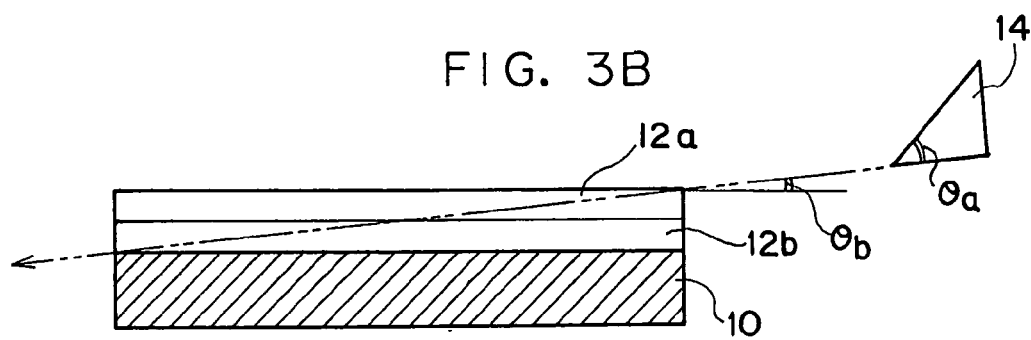
FIG. 3B is a schematic sectional view thereof.

FIG. 3A is a perspective view which schematically illustrates a state in which thin films 12a and 12b of a multilayered structure, which are formed on a support 10, are cut with a cutting edge 14 of a microtome, and FIG. 3B is a schematic sectional view thereof. In such a manner, the method of the invention can be applied to a thin film having a multilayered structure. In this case, only the cut face of the lower thin film 12b may be analyzed in the analyzing step, which will be detailed below, or only the upper thin film 12a may be analyzed, or both may be analyzed.

(2) Analyzing Step of Analyzing the Cut Section of the Thin Film

In the invention, a thin film, in particular, a thin film formed on a support is obliquely cut to form a cut section (that is, a face to be analyzed) having a sufficient area, and subsequently the presence or absence of a specific component in the cut section of the thin film is detected or the distribution state of the specific component is measured, thereby performing analysis.

The method used in the analysis is not particularly limited, and may be any method capable of qualitatively or quantitatively detecting a specific component, which is selected before hand, in the cut section in accordance with the purpose. It is advisable that the method is selected according to the type of the specific component and the required detection precision. Typical examples thereof, which can widely be used, include methods of analyzing the distribution state of the specific component of note, by (2-1) TOF-SIMS, and by (2-2) μ-ESCA. These typical detecting methods are described hereinafter.

(2-1) TOF-SIMS

In the invention, the distribution of a specific component in a thin film can be measured by cutting the thin film obliquely with a microtome and subsequently analyzing the resultant cut section of the thin film by TOF-SIMS.

An image recording layer of a planographic printing plate precursor is given as an example, and further an infrared ray absorber and a colorant are selected as specific components. In this case, the microtome cutting step and TOF-SIMS in the above-mentioned analyzing method are applied. This embodiment is described in detail hereinafter.

TOF-SIMS is the acronym for "Time-Of-Flight Secondary Ion Mass Spectrometry", and is a method of radiating primary ions, such as ions of Ga or In ($Ga^+$ or $In^+$), onto a sample to emit secondary ions, such as molecular ions or fragment ions, from the molecules in the sample, and then measuring the secondary ions, thereby measuring an image of the ions in which structure of an organic compound present in the solid surface of the sample is reflected.

The spatial resolution of the ion image in TOF-SIMS is approximately 0.1 to 0.2 μm. However, for example, the thickness of the image recording layer of an ordinary planographic printing plate precursor is as thin as approximately 1 to 2 μm; therefore, even if a section obtained by cutting the image recording layer perpendicularly to the surface of the layer is measured by TOF-SIMS, sufficient spatial resolution cannot be obtained and the distributions in the layer of the infrared ray absorber and the colorant, which are the specific components, cannot be minutely evaluated.

Therefore, a microtome is used to cut the image recording layer obliquely at an angle of 0.02 to 5° to the surface of this layer, thereby enlarging the length of the resultant cut section of the image recording layer along the depth direction of the layer by 10 to 280 times. Subsequently, it is effective to measure the cut section by TOF-SIMS, which is also is used in the present invention.

Regarding the detection of the secondary ions by TOF-SIMS, either positive ions or negative ions can be detected. In the present embodiment, positive ions are selected. In the same area in the cut section of the image recording layer, the images of all secondary ions having a mass of 0 to 1000 amu [atom mass unit] are measured in a raw data format.

In order to neutralize the charging-up of the surface of the sample being measured, an electron gun (flat gun) is used.

Measurement by TOF-SIMS is performed under the following conditions:

Device: TRIFT II manufactured by Physical Electronics (PHI) Co.
Primary ion: $Ga^{++}$ (15 kV)
Aperture: No. 3 ($Ga^{++}$ current value corresponding to 600 pA)
Mapping area: 100 to 240 μm (adjusted to a size in which the length of the cut section of the image recording layer is received)
Number of mapping points: 256×256 points
Secondary ion mass to be detected: 0 to 1000 amu (atom mossunic)
Integration time: 60 minutes Regarding the mapping data of all positive ions having a mass of 0 to 1000 amu, obtained by TOF-SIMS, a Win Cadence software Version 3.41 manufactured by Physical Electronics (PHI) Co. (hereinafter referred to as Cadence software) is used to extract ion mapping images of masses corresponding to molecular ions corresponding to cationic moieties of the infrared ray absorber and the colorant, or masses corresponding to fragment ions in which the chemical structures of the infrared ray absorber and the colorant are reflected.

When the mapping images are obtained by TOF-SIMS, spectrum-measurement is performed with milli-mass precision in a mass resolving power preferential mode (mass resolving power for $^{27}Al$: 4000 or more) in order to distinguish the target ions with certainty from ion species originating from other materials (that is, to prevent false recognition, or confusion.) In this way, with respect to the infrared ray absorber and the colorant, the following are selected: ion species having a high mass so as to reflect the chemical structure thereof as much as possible, and giving a sufficient measurement intensity (desirably, a secondary ionic strength of 10000 counts or more at the time of measuring the mapping).

The ion mapping images of the infrared ray absorber and the colorant in the same area in the cut section of the image recording layer, obtained by the above-mentioned method, are subjected to smoothing treatment using the convolve function of the Cadence software. Thereafter, the multiply function of the Cadence software is used to carry out an operation to the image data to obtain values of $\Sigma(Ai \times Bi)$, $\Sigma(Ai \times Ai)$, and $\Sigma(Bi \times Bi)$.

In this analysis example, the distribution states of the infrared ray absorber and the colorant, which are specific components, are evaluated. Steps for the evaluation are successively described hereinafter.

When the infrared ray absorber referred to as component A, the colorant referred to as component B, and further the secondary ionic strengths (count numbers) originating from component A and component B in any point (i) in the mapping area in the section of the image recording layer are represented as by Ai and Bi, respectively, the overlap between the distribution of component A and that of component B in the image recording layer can be estimated as follows: the direction cosine (cos θ) of the angle θ made by two vectors [Ai] and [Bi], which are vectors obtained when Ai and Bi are regarded as vectors.

That is, the direction cosine (cos θ) of the angle θ made by the two vectors [Ai] and [Bi] is represented by the following equation (1):

$$\cos\theta = \frac{[Ai][Bi]}{|[Ai]||[Bi]|} \quad (1)$$

wherein [Ai] [Bi] represents the inner product of the vectors [Ai] and [Bi], and |[Ai]| and |[Bi]| represent magnitudes of the vectors [Ai] and [Bi], respectively.

When the respective terms in equation (1) are represented by secondary ionic strengths Ai and Bi originating from component A (infrared ray absorber) and component B (colorant), the following can be obtained:

[Ai] [Bi]=$\Sigma(Ai \times Bi)$: the sum of the products of secondary ionic strengths of components A and B in respective points in the mapping area

|[Ai]|=√Σ(Ai×Ai): the root of the sum of the squares of secondary ionic strength (Ai) of component A in respective points in the mapping area

|[Bi]|=√Σ(Bi×Bi): the root of the sum of the squares of secondary ionic strength (Bi) of component B in respective points in the mapping area Thus, equation (1) can be converted to the following equation (2):

$$\cos\theta = \frac{\sum(Ai \times Bi)}{\sqrt{\sum(Ai \times Ai)} \times \sqrt{\sum(Bi \times Bi)}} \qquad (2)$$

In equation (2), the range of values which can be given by the cos θ is 0≦cos θ≦1. As the degree of the overlap between the distribution of component A and that of component B in the image recording layer becomes larger, the value of the cos θ becomes larger.

If the distribution of component A and that of component B overlap completely with each other in the image recording layer in accordance with the TOF-SIMS ion mapping images of components A and B, the value of the cos θ is 1, which is the largest value. On the contrary, if distribution of component A and that of component B do not overlap at all with each other, the value of the cos θ is 0, which is the smallest value.

Therefore, with respect to the TOF-SIMS ion mapping images of the infrared ray absorber and the colorant in the image recording layer section, the value of the cos θ based on equation (2) is calculated, whereby it is possible to evaluate quantitatively the degree of the overlap between the distribution of the infrared ray absorber and that of the colorant in the image recording layer.

In the present embodiment, the distribution states of the infrared ray absorber and the colorant are analyzed. By paying attention to the secondary ionic strengths (count numbers) originating from specific substances in the same way, various compounds can be analyzed.

(2-2) μ-ESCA

Another analyzing method is a method of analyzing the cut section of the thin film by μ-ESCA [X-ray Electron Spectroscopy for Chemical Analysis].

An example of measurement by μ-ESCA is described hereinafter, giving specific conditions for analyzing the infrared ray absorber and the colorant in the same way as described above.

1) Device: PHI Quantum 2000
2) X-ray source: Al—Kα (beam size (diameter): 10 to 20 μmφ)
3) Pulse energy: 58.7 eV or 93.9 eV
4) Neutralizing conditions: An electron gun and an $Ar^+$ ion gun, which provide a low acceleration (accelerating voltage: 10 eV or less), are used to neutralize the charging-up of the surface of a sample being measured.
5) Measurement: The distribution state of each component along the depth direction is quantitatively analyzed by mapping measurement and section line scanning measurement.

The above has described typical examples of the analyzing method, giving an example of the method for analyzing the distribution of the infrared ray absorber and that of the colorant as specific components. In the analyzing method of the invention, components having properties which can be distinguishable from each other as specific components are selected as described above, whereby such plural specific components can be simultaneously analyzed. A different analyzing method such as microscopic FT-IR, besides the above-mentioned method, can be used depending on the purpose if the analyzing method is suitable for properties of the specific components.

The thin film analyzing method of the invention can be applied to any thin film, and can be applied, in particular, to any thin film formed on a support. The thin film analyzing method of the invention is particularly useful for analyzing a component contained in the image recording layer of a planographic printing plate precursor.

In order to improve the scratch resistance of a planographic printing plate precursor and development latitude when an image is formed, the inventors suggested a technique for making the distribution of an infrared ray absorber and that of a colorant different from each other in its image recording layer. Incidentally, it can be easily presumed that when a low molecular weight substance is incorporated into an image recording layer, the low molecular weight substance generally moves in the layer with the passage of time in the step of applying the layer, the step of drying the layer and other steps; thus, the substance does not necessarily remain in the same layer. Accordingly, it can be presumed that even if an infrared ray absorber or a colorant is incorporated into an image recording layer, the composition of the actually-obtained image recording layer does not necessarily directly reflect the composition of an image recording layer coating solution or the structure of the image recording layer. It therefore becomes necessary to develop a method for analyzing a detailed composition distribution in the image recording layer. Thus, the invention has been made.

That is, when the analyzing method of the invention is applied to a planographic printing plate precursor comprising, on a support, an image recording layer comprising a water-insoluble and alkali-soluble resin, an infrared ray absorber, and a colorant, it is possible to analyze the in-layer distributions of the infrared ray absorber and the colorant in the layer in detail.

A more specific example of the embodiment wherein the distributions of the respective compounds are different in the image recording layer is an embodiment wherein each of the infrared ray absorber and the colorant is not uniformly distributed, and further the two compounds have centers of their distributions at different positions.

The method for analyzing the different distributions of these compounds in the image recording layer is a method of performing the cutting step of cutting the image recording layer obliquely and subsequently analyzing the cut section by TOF-SIMS or μ-ESCA, as described above. By this analysis, the in-layer distribution states of the infrared ray absorber and colorant can be understood in detail.

Another embodiment wherein the distributions of the respective compounds are different in the image recording layer is an embodiment wherein the image recording layer has a multilayered structure, and the colorant is a colorant contained in only a specific sub-layer of the multilayered structure image recording layer. Of course, the method of the invention can be applied to such a case, that is, a case in which a thin film to be analyzed has a multilayered structure.

In connection with the degree of the distributions of respective compounds in the image recording layer of a planographic printing plate precursor suggested previously, when the degree of overlap between the in-layer distributions of the infrared ray absorber and that of the colorant in the image recording layer is obtained from the following equation by analyzing the obliquely-cut section of the layer by TOM-SIMS, the value of the cos θ is preferably 0.8 or less:

$$\cos\theta = \frac{\sum(Ai \times Bi)}{\sqrt{\sum(Ai \times Ai)} \times \sqrt{\sum(Bi \times Bi)}}$$

Σ(Ai×Bi): the sum of the products of secondary ionic strengths of components A and B in respective points in the mapping area Σ(Ai×Ai): the sum of the squares of secondary ionic strength (Ai) of component A in respective points in the mapping area Σ(Bi×Bi): the sum of the squares of secondary ionic strength (Bi) of component B in respective points in the mapping area The effect of the mechanism for producing a difference between the in-layer distributions of an infrared ray absorber and that of a colorant in the image recording layer of a planographic printing plate precursor upon the development latitude and scratch resistance of the plate precursor is unclear; however, the following mechanism can be presumed.

In the planographic printing plate material for infrared ray lasers, the infrared ray absorber interacts with a binder resin in a non-exposed portion (image portion), so as to function as a dissolution inhibitor lowering the solubility of the binder resin. On the other hand, in an exposed portion (non-image portion), the generated heat weakens the interaction between the infrared ray absorber and the binder resin weak so as to have a function of dissolving the binder resin into an alkali developing solution.

The colorant in the planographic printing plate material for infrared ray lasers is a dye or pigment, the color of which is changed by laser exposure. The colorant is originally added to function as a printing-out agent capable of easily distinguishing the exposed portion and the non-exposed portion from each other base on their appearances in the step of handling the printing plate.

However, some of the colorants have a structure capable of interacting with alkali-soluble resin in the same manner as the infrared ray absorber. When any one of such colorants is used, the colorant may also interact with the binder resin in the same manner as the infrared ray absorber when the in-layer distributions of the infrared ray absorber and the colorant are uniform. In this way, there are cases where the colorant may function as a dissolution inhibitor.

When such an interaction is generated, the colorant displays no absorption wavelength within the infrared ray range, or displays a much weaker absorption than the infrared ray absorber. For this reason, the interaction between the colorant and the binder resin is maintained without being weakened even in the infrared ray laser exposed portion (non-image portion), so that the alkali-developability of the exposed portion is lowered. As a result, the development latitude is also lowered.

Even when a colorant which does not interact with the binder resin is used, interaction between the infrared ray absorber and the binder resin is three-dimensionally hindered by the colorant distributed near the infrared ray absorber when the in-layer distributions of the infrared ray absorber and the colorant are uniform. It is presumed that as a result, the development latitude is lowered.

However, by changing the in-layer distributions of the infrared ray absorber and the colorant in the image recording layer, that is, by separating the layer functionally into an area which mainly exhibits image-forming function and an area which mainly contributes to improving the strength of the layer, for example, a region where the concentration of the infrared ray absorber is higher than that of the colorant is generated in the layer, the infrared ray absorber interacts selectively or preferentially with the binder resin, so that difference in solubility between the exposed portion and the non-exposed portion becomes large. Accordingly, an image recording layer excellent in development latitude and scratch resistance can be formed. In a region where the concentration of the colorant is relatively high, film property excellent in strength is exhibited. In this way, it is presumed that the image recording layer is formed into an overall balanced, excellent image recording layer.

In order to detect the property of such an image recording layer, it is important to precisely analyze the distributions of the infrared ray absorber and the colorant in the image recording layer.

The method for generating difference between the in-layer distributions of the infrared ray absorber and the colorant in the image recording layer is not particularly limited. For example, methods described below can be given.

1. Case of Applying and Drying a Coating Solution Having a Single Composition to Form an Image Recording Layer (Image Recording Layer Having a Monolayered Structure)
(1-1) Method of selecting the infrared ray absorber and the colorant which are incompatible with each other, and using the incompatibility to produce a phase-separated structure in the applying and drying steps;
(1-2) Method of selecting the infrared ray absorber and the colorant which are different from each other in density, and using the difference to produce a phase-separated structure in the applying and drying steps;
(1-3) Method of using two binders which are incompatible with each other, in image recording layer formation, dissolving or dispersing the infrared ray absorber and the colorant into two or more binder resins which are different in compatibility, and producing a phase-separated structure of the binder resins in the applying and drying steps to incorporate the infrared ray absorber and the colorant separately into the different binder resin phases; and
(1-4) Method of introducing a structure having surface activity, such as a fluoroalipahtic group, an aliphatic group having a siloxane structure, or a polyoxyalkylene group, into either one of the infrared ray absorber and the colorant, thereby distributing either one of the infrared ray absorber and the colorant, either of which has the surface activity group, unevenly near the surface in the applying and drying steps.

2. Case of Applying and Drying Coating Solutions Having Different Compositions to Form an Image Recording Layer Having a Multilayered Structure (Image Recording Layer Having a Multilayered Structure)
(2-1) Method of using two or more coating solutions wherein the concentrations of the infrared ray absorber and the colorant in a binder for forming a coating are different, and applying and drying the coating solutions successively or simultaneously (multilayer coating).

The above-mentioned methods can be given.

The format of the in-layer distributions of the infrared ray absorber and the colorant is not particularly limited as long as the concentration ratio between the infrared ray absorber and the colorant is not uniform in the image recording layer.

Examples include: distributing the infrared ray absorber and the colorant into regions which are entirely different;

distributing one of the infrared ray absorber and the colorant into the whole image recording layer, and distributing only the other unevenly into some region in the image recording layer or distributing the other so as to have a concentration gradient in the image recording layer; and distributing both the infrared ray absorber and the colorant into the whole image recording layer so as to have different concentration gradients.

Examples of the system in which the in-layer distributions of the infrared ray absorber and the colorant are different include: a system in which the concentration distributions are different in a lamellar form; a system in which the concentration distributions are different in a phase-separated form (sea-island structure form); and a system in which the lamellar form and the phase-separated form are mixed.

A more preferable example of the distributions of the infrared ray absorber and the colorant in the image recording layer is a system in which a region where the solubilities of an exposed portion and a non-exposed portion are largely different is formed near the interface between the image recording layer and the support. In this system, the exposed portion (non-image portion) is quickly dissolved in an alkali developing solution. As a result, the development latitude of the printing plate precursor can be expected to improve.

Conversely, according to a system in which a region where the difference between the solubilities of an exposed portion and a non-exposed portion is small is formed near the surface contacting the air, resistance against developing solution or external stress is improved. Thus, the development latitude and the scratch resistance can be expected to improve.

For this reason, it is preferable that the infrared ray absorber is placed near the surface of the support and the colorant is distributed above the infrared ray absorber (near the surface contacting the air).

The cos θ is preferably 0.8 or less, more preferably 0.75 or less, and still more preferably 0.37 or less.

The following describes in detail the image recording layer of a planographic printing plate precursor, which is a thin film to which the analyzing method of the invention can be preferably applied. As respective components which constitute the image recording layer (for example, a water-insoluble and alkali-soluble resin, an infrared ray absorber, and a colorant), components which are known and widely used for conventional planographic printing plate precursors can be used.

Examples of the water-insoluble and alkali-soluble resin which can be used in the image recording layer related to the invention (hereinafter referred to as the alkali-soluble resin as the case may be) include homopolymers each containing, in the main chain or a side chain thereof, an acidic group, and copolymers thereof, and mixtures thereof.

Among these examples, polymers each containing, in the main chain and/or a side chain thereof, an acidic group described in each of the following items (1) to (6) are preferable from the viewpoints of the solubility thereof in alkali developing solution and the expression of dissolution-suppressing function:

(1) phenol group (—Ar—OH),
(2) sulfonamide group (—SO$_2$NH—R),
(3) substituted sulfonamide group (hereinafter referred to as an "active imide group"), such as —SO$_2$NHCOR, —SO$_2$NHSO$_2$R, or —CONHSO$_2$R,
(4) carboxylic acid group (—CO$_2$H),
(5) sulfonic acid group (—SO$_3$H), and
(6) phosphoric acid group (OPO$_3$H$_2$).

In the above items (1) to (6), Ar represents a bivalent aryl linking group which may have a substituent, and R represents a hydrogen atom or a hydrocarbon group which may have a substituent.

Among the alkali-soluble resins having an acidic group selected from items (1) to (6), preferable are alkali-soluble resins having (1) a phenol group, (2) a sulfonamide group or (3) an active imide group. Most preferable are alkali-soluble resins having (1) a phenol group or (2) a sulfonamide group in order to sufficiently maintain the solubility in alkali developing solution, the development latitude, and the film strength of the image recording layer.

Compounds having acidic group (1), (2) or (3), which are preferable examples of the alkali-soluble resin having an acidic group, are described in detail.

(1) Examples of the alkali-soluble resin having a phenol group include novolak resins such as polycondensation products of phenol and formaldehyde, polycondensation products of m-cresol and formaldehyde, polycondensation products of p-cresol and formaldehyde, polycondensation products of m-/p-mixed cresol and formaldehyde, and polycondensation products of phenol, cresol (m-cresol, p-cresol, or m-/p-mixed cresol) and formaldehyde; polycondensation products of pyrogallol and acetone; copolymers obtained by copolymerizing a compound having in a side chain thereof a phenol group. Examples of the compound having a phenol group include acrylamide, methacrylamide, acrylate acid ester and methacrylate acid ester which each have a phenol group, and hydroxystyrene.

(2) Examples of the alkali-soluble resin having a sulfonamide group include polymers each comprising, as a main constituent, a minimum constituting unit originating from a compound having a sulfonamide group. Examples of such a compound include compounds each having, in the molecule thereof, a sulfonamide group —NH—SO$_2$, wherein at least one hydrogen atom is bonded to a nitrogen atom, and a polymerizable unsaturated group. Among these compounds, preferable are low molecular compounds each having, in the molecule thereof, an acryloyl group, an allyl group or a vinyloxy group, and a substituted or mono-substituted aminosulfonyl group or a substituted sulfonylimino group.

(3) Examples of the alkali-soluble resin having an active imide group include polymers each comprising, as a main constituent, a minimum constituting unit originating from a compound having an active imide group. Examples of such a compound include compounds each having, in the molecule thereof, one or more active imide groups and one or more polymerizable unsaturated groups.

Specifically, preferable examples thereof include N-(p-toluenesulfonyl)methacrylamide and N-(p-toluenesulfonyl)acrylamide.

Regarding the minimum constituting unit having an acidic group selected from items (1) to (6), which constitutes the alkali-soluble resin, it is not necessarily essential to use a single kind thereof. Thus, it is acceptable to use two or more kinds of minimum constituting units having the same acidic group or two or more kinds of minimum constituting units having different acidic groups, or to use the minimum constituting unit together with a different constituting unit having no acidic group (as a copolymerizable unit). Particularly preferable are polymers obtained by polymerizing the constituting unit having acidic group (1) with two or more kinds of monomers having acidic group (2) or (3), and copolymers obtained by copolymerizing these monomers further with some other monomer. In the case that the constituting unit having acidic group (1) is copolymerized with the monomer having acidic group (2) or (3), the blend ratio between the unit and the monomer is preferably from 50:50 to 5:95, and more preferably from 40:60 to 10:90.

As for the above-mentioned copolymer, the compound to be copolymerized has an acidic group selected from items (1) to (6), and is contained in the copolymer preferably in an amount of 10% by mole, and more preferably in an amount of 20% or more. If the amount is less than 10% by mole, there is a tendency that the development latitude is unable to be sufficiently improved.

In the case that a compound is copolymerized to prepare the alkali-soluble resin and this resin is used as a copolymer, a different compound having none of the acidic groups described in items (1) to (6) can be used as the compound to be copolymerized. The different compound is not limited, and examples thereof include compounds described in the following items (m1) to (m12):

(m1) acrylic acid esters andmethacrylic acid esters each having an aliphatic hydroxyl group, such as 2-hydroxyethyl acrylate or 2-hydroxyethyl methcrylate;

(m2) alkyl acrylates such as methyl acrylate, ethyl acrylate, propyl acrylate, butyl acrylate, amyl acrylate, hexyl acrylate, octyl acrylate, benzyl acrylate, 2-chloroethyl acrylate, and glycidyl acrylate;

(m3) alkyl methacrylates such as methyl methmethacrylate, ethyl methacrylate, propyl methacrylate, butyl methacrylate, amyl methacrylate, hexyl methacrylate, cyclohexyl methacrylate, benzyl methacrylate, 2-chloroethyl methacrylate, and glycidyl methacrylate;

(m4) acrylamides or methacrylamides such as acrylamide, methacrylamide, N-methylolacrylamide, N-ethylacrylamide, N-hexylmethacrylamide, N-cyclohexylacrylamide, N-hydroxyethylacrylamide, N-phenylacrylamide, N-nitrophenylacrylamide, and N-ethyl-N-phenylacrylamide;

(m5) vinyl ethers such as ethyl vinyl ether, 2-chloroethyl vinyl ether, hydroxyethyl vinyl ether, propyl vinyl ether, butyl vinyl ether, octyl vinyl ether, and phenyl vinyl ether;

(m6) vinyl esters such as vinyl acetate, vinyl chloroacetate, vinyl butyrate, and vinyl benzoate;

(m7) styrenes such as styrene, α-methylstyrene, methylstyrene, and chloromethylstyrene;

(m8) vinyl ketones such as methyl vinyl ketone, ethyl vinyl ketone, propyl vinyl ketone, and phenyl vinyl ketone;

(m9) olefins such as ethylene, propylene, isobutylene, butadiene, and isoprene;

(m10) N-vinylpyrrolidone, acrylonitrile, and methacrylonitrile;

(m11) unsaturated imides such as maleimide, N-acryloylacrylamide, N-acetylmethacrylamide, N-propionylmethacrylamide, N-(p-chlorobenzoyl)methacrylamide; and (m12) unsaturated carboxylic acids such as acrylic acid, methacrylic acid, maleic anhydride, and itaconic acid.

The weight average molecular weight of the alkali-soluble resin is preferably 500 or more, and more preferably from 1,000 to 700,000 from the viewpoint of image forming ability. The number average molecular weight thereof is preferably 200 or more, and more preferably from 750 to 650,000. More specifically, when the alkali-soluble resin is a polymer comprising a constituting unit having acidic group (1), (2) or (3), the weight average molecular weight is preferably from 5,000 to 30,000, the number-average molecular weight is preferably from 800 to 250,000 and the dispersion degree (weight average molecular weight/number-average molecular weight) is preferably from 1.1 to 10. When the alkali-soluble resin is a phenol-formaldehyde resin or a cresol resin, the weight average molecular weight is preferably from 500 to 20,000 and the number average molecular weight is preferably from 200 to 10,000.

These alkali-soluble resins may be used alone or in combination of two or more thereof.

The content of the alkali-soluble resin in the image recording layer preferably used in the invention is preferably from 30 to 98%, more preferably from 40 to 95%, and still more preferably from 50 to 90% by mass of all solid contents in the image recording layer from the viewpoints of printing resistance, sensitivity, and image forming ability.

[Infrared Ray Absorber]

The infrared ray absorber used in the image recording layer related to the invention is not particularly limited, and may be a dye which absorbs infrared rays used for recording and generates heat. Preferable examples thereof include infrared ray absorbing dyes and infrared ray absorbing pigments having an absorption maximum within a wavelength range of 760 to 1200 nm from the viewpoint of the suitability thereof for easily obtainable high-power lasers.

As such an infrared ray absorber, the following can be used: commercially available dyes, and known dyes described in publications such as "Dye Handbook" (edited by the Society of Synthesis Organic Chemistry, Japan and published in 1970), specific examples of which include azo dyes, metal complex salt azo dyes, pyrrozolone azo dyes, naphotoquinone dyes, anthraquinone dyes, phathalocyanine dyes, carbonium dyes, quinoneiminedyes, methinedyes, cyaninedyes, squaryliumdyes, pyrylium salts, metal thiolate complexes, oxonol dyes, diimmonium dyes, diimonium dyes, and aminium dyes.

Preferable examples of the dyes include cyanine dyes described in JP-A Nos. 58-125246, 59-84356, 59-202829, and 60-78787; methine dyes described in JP-A Nos. 58-173696, 58-181690 and 58-194595; naphtoquinone dyes described in JP-A Nos. 58-112793, 58-224793, 59-48187, 59-73996, 60-52940, and 60-63744; squarylium dyes described in JP-A No. 58-112792; and cyanine dyes described in U.K. Patent No. 434, 875.

Other preferable examples of the infrared ray absorber include near infrared ray sensitizers described in U.S. Pat. No. 5,156,938, substituted aryl benzo(thio)pyrylium salts described in U.S. Pat. No. 3,881,924, trimethine thiapyrylium salts described in JP-A No. 57-142645 (corresponding to U.S. Pat. No. 4,327,169), pyrylium compounds described in JP-A Nos. 58-181051, 58-220143, 59-41363, 59-84248, 59-84249, 59-146063 and 59-146061, cyanine dyes described in JP-A No. 59-216146, pentamethine thiopyrylium salts described in U.S. Pat. No. 4,283,475, and pyrylium compounds described in JP-B Nos. 5-13514 and 5-19702. Particularly preferable examples thereof include commercially available products such as Epolight III-178, Epolight III-130, and Epolight III-125 by Epoline Corp.

Additional preferable examples of the dye include near infrared ray absorbing dyes represented by formula (I) or (II) indicated in U.S. Pat. No. 4,756,993.

Examples of a pigment used as the infrared ray absorber in the present invention include commercially available pigments and pigments described in "Color Index (C.I.) Handbooks", "Latest Pigment Handbook" (edited by the Society of Pigment Technology, Japan, and published in 1977), "Latest Pigment Applied Technology" (published by CMC Publishing Co., Ltd. in 1986), and "Printing Ink Technology" (published by CMC Publishing Co., Ltd. in 1984).

Examples of the types of the pigment include black pigment, yellow pigment, orange pigment, brown pigment, red pigment, purple pigment, blue pigment, green pigment, fluorescent pigment, metal powder pigment, and polymer-bonded dye. Specific examples thereof include insoluble azo pigment, azo lake pigment, condensed azo pigment, chelate azo pigment, phthalocyanine pigment, anthraquinone pigment, perylene and perylene pigment, thioindigo pigment, quinacridon pigment, dioxazine pigment, isoindolinone pigment, quinophthalone pigment, vat lake pigment, azine pigment, nitroso pigment, nitro pigment, natural pigment, fluorescent pigment, inorganic pigment, and carbon black. Details of these pigments are described in detail in JP-A No. 10-39509, paragraphs [0052] to [0054]. These pigments can be used in the present invention. Among these pigments, carbon black is preferable.

The infrared ray absorber can be added to the image recording layer in an amount of 0.01 to 50%, preferably 0.1 to 30%, and more preferably 0.5 to 10% by mass of all solid contents which constitute the image recording layer from the viewpoints of sensitivity and uniformity of the layer, strength of the layer, and others.

The preferable added amount is a total amount in the image recording layer. When the infrared ray absorber is added to the image recording layer or an adjacent layer thereof, it is necessary that the infrared ray absorber is added so as to have a distribution different from that of a colorant, which will be detailed below.

[Colorant]

It is necessary to add, to the image recording layer of the invention, a dye or pigment as an image colorant for to clearly disting the exposed portion from the non-exposed portion with the naked eye. As the image colorant, a dye other than salt-forming organic dyes is used as a printing-out agent (thermally color-developing dye added to obtain a visible image immediately after heating by exposure to light), which will be detailed later. Preferable examples of the dye include oil-soluble dyes and basic dyes. Specific examples thereof include Oil Yellow #101, Oil Yellow #103, Oil Pink #312, Oil Green BG, Oil Blue BOS, Oil Blue #603, Oil Black BY, Oil Black BS and Oil Black T-505 (all of which are manufactured by Orient Chemical Industry Ltd.), Victoria Pure Blue, Crystal Violet (CI42555), Methyl Violet (CI42535), Ethyl Violet, Rhodamine B (CI145170B), Malachite Green (CI42000), and Methylene Blue (CI52015). Dyes described in JP-A No. 62-293247 are particularly preferable.

This dye can be added in an amount of 0.01 to 10%, and preferably 0.1 to 3% by mass of all solid contents in the image forming materials which constitute the planographic printing plate. This dye is generally added to the image recording layer. When the image recording layer has a multilayered structure, the dye may be added to only one specific layer of the multilayered structure or to all of the plural layers. The dye must be added so as to have a distribution different from that of the infrared ray absorber.

In order to heighten the inhibition of the dissolution of the recording layer in alkali developing solution, various dissolution inhibiting compounds (inhibitors) can be added to the image recording layer related to the invention. The types of the dissolution inhibiting compounds are not particularly limited, and examples thereof include quaternary ammonium salts and polyethylene glycol compounds.

The types of the quaternary ammonium salts are not particularly limited, and examples thereof include tetraalkylammonium salts, trialkylarylammonium salts, dialkyldiarylammonium salts, alkyltriarylammonium salts, tetraarylammonium salts, cyclic ammonium salts and bicyclic ammonium salts.

Specific examples thereof include tetrabutylammonium bromide, tetrapentylammonium bromide, tetrahexylammonium bromide, tetraoctylammonium bromide, tetralaurylammonium bromide, tetraphenylammonium bromide, tetranaphthylammonium bromide, tetrabutylammonium chloride, tetrabutylammonium iodide, tetrastearylammonium bromide, lauryltrimethylammonium bromide, stearyltrimethylammonium bromide, behenyltrimethylammonium bromide, lauryltriethylammonium bromide, phenyltrimethylammonium bromide, 3-trifluoromethylphenyltrimethylammonium bromide, benzyltrimethylammonium bromide, dibenzyldimethylammonium bromide, distearyldimethylammonium bromide, tristearylmethylammonium bromide, benzyltriethylammonium bromide, hydroxyphenyltrimethylammonium bromide, and N-methylpyridinium bromide.

The solid content amount of the added quaternary ammonium salt is preferably from 0.1 to 50%, and more preferably from 1 to 30% by mass of all solid contents in the image recording layer, considering effects on the dissolution inhibiting effect and film property.

The types of the polyethylene glycol compound is not particularly limited, and an example thereof is a compound having the following structure:

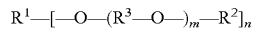

wherein $R^1$ represents a polyhydric alcohol residue or a polyhydric phenol residue; $R^2$ represents a hydrogen atom, or an alkyl, alkenyl, alkynyl, alkyloyl, aryl, or aryloxy group, each of which may have a substituent having 1 to 25 carbon atoms; $R^3$ represents an alkylene residue which may have a substituent; m is 10 or more on average; and n is an integer of 1 to 4.

Examples of the polyethylene glycol compound having the above-mentioned structure include polyethylene glycols, polypropylene glycols, polyethylene glycol alkyl ethers, polypropylene glycol alkyl ethers, polyethylene glycol aryl ethers, polypropylene glycol aryl ethers, polyethylene glycol alkyl aryl ethers, polypropylene glycol alkyl aryl ethers, polyethylene glycol glycerin ether, polypropylene glycol glycerin ethers, polyethylene sorbitol ethers, polypropylene glycol sorbitol ethers, polyethylene glycol aliphatic acid esters, polypropylene glycol aliphatic acid esters, polyethylene glycolized ethylenediamines, polypropylene glycolized ethylenediamines, polyethylene glycolized diethylenetriamines, and polypropylene glycolized diethylenetriamines.

Specific examples thereof include polyethylene glycol 1000, polyethylene glycol 2000, polyethylene glycol 4000, polyethylene glycol 10000, polyethylene glycol 20000, polyethylene glycol 50000, polyethylene glycol 100000, polyethylene glycol 200000, polyethylene glycol 500000, polypropylene glycol 1500, polypropylene glycol 3000, polypropylene glycol 4000, polyethylene glycol methyl ether, polyethylene glycol ethyl ether, polyethylene glycol phenyl ether, polyethylene glycol dimethyl ether, polyethylene glycol diethyl ether, polyethylene glycol diphenyl ether, polyethylene glycol lauryl ether, polyethylene glycol dilauryl ether, polyethylene glycol nonyl ether, polyethylene glycol cetyl ether, polyethylene glycol stearyl ether, polyethylene glycol distearyl ether, polyethylene glycol behenyl ether, polyethylene glycol dibehenyl ether, polypropylene glycol methyl ether, polypropylene glycol ethyl ether, polypropylene glycol phenyl ether, polypropylene glycol dimethyl ether, polypropylene glycol diethyl ether, polypropylene glycol diphenyl ether, polypropylene glycol lauryl ether, polypropylene glycol dilauryl ether, polypropylene glycol nonyl ether, polyethylene glycol acetyl ester, polyethylene glycol diacetyl ester, polyethylene glycol benzoic acid ester, polyethylene glycol lauryl ester, polyethylene glycol dilauryl ester, polyethylene glycol nonylic acid ester, polyethylene glycol cetylic acid ester, polyethylene glycol stearoyl ester, polyethylene glycol distearoyl ester, polyethylene glycol behenic acid ester, polyethylene glycol dibehenic acid ester, polypropylene glycol acetyl ester, polypropylene glycol diacetyl ester, polypropylene glycol benzoic acid ester, polypropylene glycol dibenzoic acid ester, polypropylene glycol lauric acid ester, polypropylene glycol dilauric ester, polypropylene glycol nonylic acid ester, polyethylene glycol glycerin ether, polypropylene glycol glycerin ether, polyethylene glycol sorbitol ether, polypropylene glycol sorbitol ether, polyethylene glycolized ethylenediamine, polypropylene glycolized ethylenediamine, polyethylene glycolized diethylenetriamine, polypropylene glycolized diethylenetriamine, and polyethylene glycol pentamethylenehexamine.

The solid content amount of the polyethylene glycol compound added is preferably from 0.1 to 50%, and more preferably from 1 to 30% of all solid contents in the image recording layer from the viewpoints of dissolution inhibiting effect and image forming ability.

When measures are taken to for improve the inhibition (dissolution inhibition), the sensitivity falls. In this case, it is effective to add a lactone compound. It appears that when developing solution permeates the exposed portion, this lactone compound and the developing solution react with each other to generate a carboxylic acid compound newly, whereby the lactone compound contributes to the dissolution of the exposed portion and improves the sensitivity.

The typed of the lactone compound is not particularly limited, and an example thereof is a compound represented by the general formula (L-I) or (L-II):

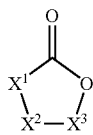

General formula (L-1)

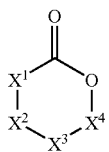

General formula (L-II)

In general formulae (L-I) and (L-II), $X^1$, $X^2$, $X^3$ and $X^4$, which may be the same or different, each have an atom or atomic group constituting the ring and may each independently have a substituent. At least one of $X^1$, $X^2$ and $X^3$ in general formula (L-I) has an electron withdrawing substituent or a substituent substituted with an electron withdrawing group, and similarly at least one of $X^1$, $X^2$, $X^3$ and $X^4$ in general formula (L-II) has an electron withdrawing substituent or a substituent substituted with an electron withdrawing group.

The ring-constituting atoms or atomic groups represented by $X^1$, $X^2$, $X^3$ and $X^4$ are each a nonmetallic atom or an atomic group comprising a nonmetallic atom, the atom or atomic group having two single bonds to form the ring.

Preferable examples of the nonmetallic atom or the nonmetallic atomic group are atoms or atomic groups selected from a methylene group, a sulfinyl group, a carbonyl group, a thiocarbonyl group, a sulfonyl group, a sulfur atom, an oxygen atom, and a selenium atom. More preferably examples thereof are atomic groups selected from methylene, carbonyl and sulfonyl groups.

At least one of $X^1$, $X^2$ and $X^3$ in general formula (L-I) or at least one of $X^1$, $X^2$, $X^3$ and $X^4$ in general formula (L-II) has an electron withdrawing group. The electron withdrawing substituent in the present specification means a group having a positive Hammett substituent constant σp. With regard to the Hammett substituent constant, the following can be referred to: Journal of Medicinal Chemistry, 1973, Vol. 16, No. 11, 1207–1216, and so on.

Examples of the electron withdrawing group having a positive Hammett substituent constant σp include halogen atoms (such as a fluorine atom (σp value: 0.06), a chlorine atom (σp value: 0.23), a bromine atom (σp value: 0.23) and a iodine atom (σp value: 0.18)); trihaloalkyl groups (such as tribromomethyl (σp value: 0.29), trichloromethyl (σp value: 0.33), and trifluoromethyl (σp value: 0.54)); a cyano group (σp value: 0.66); a nitro group (σp value: 0.78); aliphatic, aryl or heterocyclic sulfonyl groups (such as methanesulfonyl (σp value: 0.72)); aliphatic, aryl or heterocyclic acyl groups (such as acetyl (σp value: 0.50) and benzoyl (σp value: 0.43)); alkynyl groups (such as C≡CH (σp value: 0.23)); aliphatic, aryl or heterocyclic oxycarbonyl groups (such as methoxycarbonyl (σp value: 0.45) and phenoxycarbonyl (σp value: 0.44)); and a carbamoyl group (σp value: 0.36); a sulfamoyl group (σp value: 0.57); a sulfoxide group; heterocyclic groups; an oxo group; and a phosphoryl groups.

Preferable examples of the electron withdrawing group include an amide group, an azo group, a nitro group, fluoroalkyl groups having 1 to 5 carbon atoms, a nitrile group, alkoxycarbonyl groups having 1 to 5 carbon atoms, acyl groups having 1 to 5 carbon atoms, alkylsulfonyl groups having 1 to 9 carbon atoms, arylsulfonyl groups having 6 to 9 carbon atoms, alkylsulfinyl groups having 1 to 9 carbon atoms, arylsulfinyl groups having 6 to 9 carbon atoms, arylcarbonyl groups having 6 to 9 carbon atoms, thiocarbonyl groups, fluorine-containing alkyl groups having 1 to 9 carbon atoms, fluorine-containing aryl groups having 6 to 9 carbon atoms, fluorine-containing allyl groups having 3 to 9 carbon atoms, an oxo group, and halogen atoms.

More preferable examples of the electron withdrawing group include a nitro group, fluoroalkyl groups having 1 to 5 carbon atoms, a nitrile group, alkoxycarbonyl groups having 1 to 5 carbon atoms, acyl groups having 1 to 5 carbon atoms, arylsulfonyl groups having 6 to 9 carbon atoms, arylcarbonyl groups having 6 to 9 carbon atoms, an oxo group, and halogen atoms.

Specific examples of the compound represented by general formula (L-I) or general formula (L-II) are given below. In the invention, however, the compound is not limited to these examples.

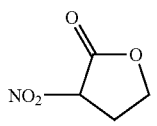 (LI-1)
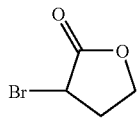 (LI-2)
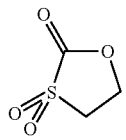 (LI-3)
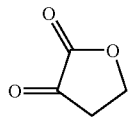 (LI-4)
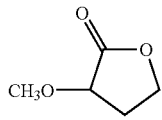 (LI-5)
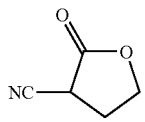 (LI-6)
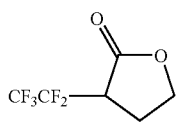 (LI-7)
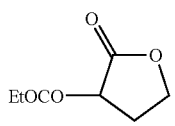 (LI-8)
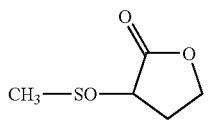 (LI-9)
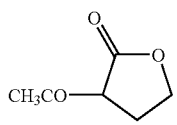 (LI-10)
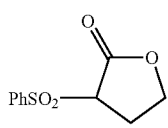 (LI-11)
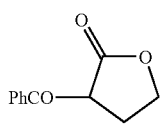 (LI-12)
-continued
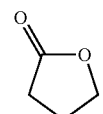 (LI-13)
(LI-14)
(LI-15)
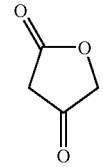 (LI-16)
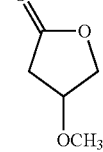 (LI-17)
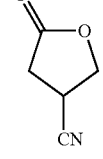 (LI-18)
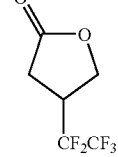 (LI-19)
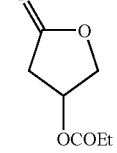 (LI-20)
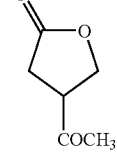 (LI-21)

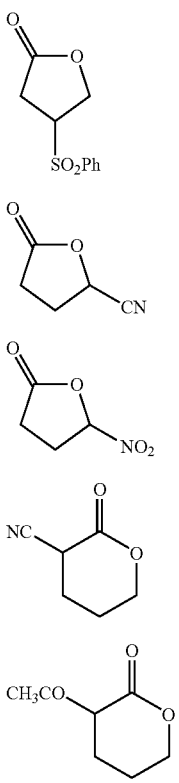

The solid content amount of the added compound represented by general formula (L-I) or general formula (L-II) is preferably from 0.1 to 50%, and more preferably from 1 to 30% by mass of all solid contents in the image recording layer. If the amount is less than 0.1%, the advantageous effect is small. If the amount is more than 50%, the image-forming ability is poor. Since this compound reacts with developing solution, it is desired that the compound selectively contacts the developing solution These lactone compounds may be used alone or in combination. Two or more of the compounds represented by general formula (L-I), or two or more of the compounds represented by general formula (L-II) may be used at an arbitrary ratio if the total amount of the lactone compounds added is within the above-mentioned ranges.

In order to make the difference between the exposed portion and the non-exposed portion larger, it is preferable that the image recording layer of the invention further contains a substance which can be thermally decomposed and which substantially inhibits the solubility of the alkali-soluble resin in a state wherein the substance is not thermally decomposed.

The type of the "substance which can be thermally decomposed and which substantially inhibits the solubility of the alkali-soluble resin in a state wherein the substance is not thermally decomposed" is not particularly limited, and examples thereof include various onium salts and quinonediazide compounds. Onium salts are particularly preferable from the viewpoint of the thermally decomposing property thereof.

Examples of the onium salts include diazonium salts, ammonium salts, phosphonium salts, iodonium salts, sulfonium salts, selenium salts, and arsenium salts. Preferable examples of the onium salt used in the invention include diazonium salts described in S. I. Schlesinger, Photogr. Sci. Eng., 18, 387 (1974), T. S. Bal et al., Polymer, 21, 423 (1980) and JP-A No. 5-158230, ammonium salts described in U.S. Pat. Nos. 4,069,055, 4,069,056 and Re 27,992, and Japanese Patent Application No. 3-140140, phosphonium salts described in D. C. Necker et al., Macromolecules, 17, 2468 (1984), C. S. Wen et al., Teh, Proc., Conf. Rad. Curing ASIA, p.478, Tokyo, Oct (1988), and U.S. Pat. Nos. 4,069,055 and 4,069,056, sulfonium salts described in J. V. Crivello et al., Macromolecules, 10(6), 1307 (1977), Chem & Eng. News, Nov. 28, p.31 (1988), EP No. 104, 143, U.S. Pat. Nos. 5,041,358, 4,491,628, 4,760,013, 4,734,444 and 2,833, 827, German Patent Nos. 2,904,626, 3,604,580, and 3,604, 581, selenium salts described in J. V. Crivello et al., Macromolecules, 10(6), 1307 (1977), and J. V. Crivello et al., J. Polymer Sci., Polymer Chem. Ed., 17, 1047 (1979), and arsenium salts described in C. S. Wen et al., Teh, Proc. Conf. Rad. Curing ASIA, p.478 Tokyo, Oct (1988).

Among the onium salts, diazonium salts are particularly preferable. Particularly preferable examples of the diazonium salts are salts described in JP-A No. 5-158230.

Examples of the counter ion for the onium salt include tetrafluoroboric acid, hexafluorophosphoric acid, triisopropylnaphthalenesulfonic acid, 5-nitro-o-toluenesulfonic acid, 5-sulfosalicylic acid, 2,5-dimethylbenzenesulfonic acid, 2,4, 6-trimethylbenzenesulfonic acid, 2-nitrobenzenesulfonic acid, 3-chlorobenzenesulfonic acid, 3-bromobenzene-sulfonic acid, 2-fluorocaprylnaphthalenesulfonic acid, dodecylbenzenesulfonic acid, 1-naphthol-5-sulfonic acid, 2-methoxy-4-hydroxy-5-benzoyl-benzenesulfonic acid, and paratoluenesulfonic acid ions. Among these examples, alkylaromatic sulfonic acid ions are preferable, examples of which include hexafluorophosphoric acid, triisopropylnaphthalenesulfonic acid, and 2,5-dimethylbenzenesulfonic acid ions.

The amount of the onium salts added is preferably from 0.1 to 50%, more preferably from 0.1 to 30%, and still more preferably from 0.3 to 30% by mass of all solid contents in the image recording layer. The onium salts may be used alone or in a mixture form.

The quinonediazide compounds are preferably o-quinonediazide compounds. The o-quinonediazide compound used in the invention is a compound having at least one o-quninonediazide group and having alkali-solubility increased by thermal decomposition. The compound may have various structures. That is, the o-quinonediazide assists the dissolution of the sensitive material system by both of the following effects: an effect in which the o-quinonediazide is thermally decomposed, whereby its capability of suppressing the dissolution of the binder is lost; and an effect in which the o-quinonediazide itself changes to an alkali-soluble substance. Examples of the o-quinonediazide compound used in the invention may be compounds described in J. Kosar's "Light-Sensitive Systems" (John Wiley & Sons. Inc.), pp. 339–352. Preferable examples thereof include sulfonates or sulfonamides of o-quinonediazide reacting with any one of various aromatic polyhydroxyl compounds and aromatic amino compounds. Other examples thereof include esters made from benzoquinone-(1,2)-diazide sulfonic acid chloride or naphthoquinone-(1,2)-diazide-5-sulfonic acid chloride andpyrogallol-acetone resin, as described in JP-B No. 43-28403; and esters made from benzoquinone-(1,2)-diazide sulfonic acid chloride or naphthoquinone-(1, 2)-diazide-5-sulfonic acid chloride and phenol-formaldehyde resin, as described in U.S. Pat. Nos. 3,046,120 and 3,188,210.

Additional preferable examples of the o-quinonediazide compound used in the invention include esters made from naphthoquinone-(1,2)-diazide-4-sulfonic acid chloride and phenol-formaldehyde resin or cresol-formaldehyde resin; and esters made from naphthoquinone-(1,2)-diazide-4-sulfonic acid chloride and pyrogallol-acetone resin. Other useful examples of the o-quinonediazide compounds are described in patent-related documents, examples of which include JP-A Nos. 47-5303, 48-63802, 48-63803, 48-96575, 49-38701 and 48-13354, JP-B Nos. 41-11222, 45-9610 and 49-17481, U.S. Pat. Nos. 2,797,213, 3,454,400, 3,544,323, 3,573,917, 3,674,495 and 3,785,825, U.K. Patent Nos. 1,227,602, 1,251,345, 1,267,005, 1,329,888 and 1,330,932, and German Patent No. 854,890.

The amount of the o-quinonediazide compounds added is preferably from 1 to 50%, more preferably from 5 to 30%, and still more preferably from 10 to 30% by mass of all solid contents in the image recording layer. The o-quinonediazide compounds may be used alone or in a mixture form.

Among the above-mentioned examples, the onium salt compound is preferable from the viewpoint of the decomposing property thereof. It appears that the addition of the onium salt, which has good thermally-decomposing property, makes it possible to promote decomposition of the thermally-decomposing substance in the exposed portion so as to improve the discrimination of this portion.

The image recording layer of the invention is formed on an appropriate support so as to constitute a planographic printing plate precursor. The image recording layer may have a monolayered structure, or a multilayered structure composed of plural layers having different compositions.

In the case of the monolayered structure, an image recording layer coating solution comprising the above-mentioned respective components and optional components, which will be detailed later, is applied onto a support and is dried. In this case, it is necessary to adopt the measure of considering physical properties of the infrared ray absorber and the colorant to make the distribution of the infrared ray absorber and that of the colorant different, the measure of using two binders incompatible with each other to form a phase-separated structure in the single layer, the measure of introducing a structure having surface activity to any one of the infrared ray absorber and the colorant, and other measures, as described above.

The following describes the case that the image recording layer has a multilayered structure, giving as an example an image recording layer having a bilayered structure for the sake of convenience. (Hereinafter, the layer near a support and the layer positioned at the surface side are referred to as the lower layer and the upper layer, respectively.)

In the case of forming the image recording layer having the multilayered structure, it is preferable that alkali-soluble resins different from each other are used for the upper layer and the lower layer in order to prevent compatibility with the two layers in the interface therebetween. From the viewpoint of image forming ability, it is preferable to use, for the upper layer, a resin having lower solubility in alkali aqueous solution than the resin for the lower layer.

In the case of forming the multilayered structure, it is allowable to apply the lower layer and dry the layer, and subsequently form the upper layer, or to form the two layers by multicoating.

In the case of adding the infrared ray absorber and the colorant, it is permissible to add different compounds for the respective layers, to add different combinations of plural compounds for the respective layers, or to add the infrared ray absorber and the colorant so as to contain different amounts for the respective layers. Attention should be paid so that the total amount of the infrared ray absorber or the colorant added to the plural layers is within the above-mentioned preferable ranges. In order to make the distribution of the infrared ray absorber and that of the colorant different from each other, the infrared ray absorber and the colorant may be added to different layers.

It is feared that the "substance which can be thermally decomposed and which substantially inhibits the solubility of the alkali-soluble resin in a state wherein the substance is not thermally decomposed" is thermally decomposed slightly with the passage of time. Hence, when adding the substance to the image recording layer having the multilayered structure, it is effective to add the substance to the lower layer. Needless to say, however, the substance may be added to the upper layer or the two layers.

[Other Components]

When the image recording layer of the invention is formed, various additives may be added optionally thereto as long as the effect of the layer is not damaged. The following describes the additives, giving examples thereof.

In order to improve the discrimination between the image portion and the non-image portion, or to improve the scratch resistance of the image recording layer, it is preferable to use, in this layer, a polymer made from a (meth)acrylate polymerizable monomer having, in the molecule thereof, two or three perfluoroalkyl groups having 3 to 20 carbon atoms, as a constituting unit, as described in JP-A No. 2000-187318. In the case of the multilayered structure, such a compound may be added to any one of the layers. It is effective to add the compound to the upper layer.

The amount of the added polymer is preferably from 0.1 to 10%, and more preferably from 0.5 to 5% by mass of all solid contents in the image recording layer.

In order to provide a higher scratch resistance to the image recording layer, a compound for lowering the coefficient of static friction of the surface may be added. Specific examples thereof include long-chain alkylcarboxylic acid esters as described in U.S. Pat. No. 6,117,913. In the case of the multilayered structure, such a compound may be added to any one of the layers. It is effective to add the compound to the upper layer.

The amount of the added compound is preferably from 0.1 to 10%, and more preferably from 0.5 to 5% by mass of all solid contents in the image recording layer.

If necessary, a compound having a low molecular weight acidic group may be added. Examples of the acidic group include sulfonic acid, carboxylic acid, and phosphoric acid. Among these examples, compounds having a sulfonic acid are preferable. Specific examples thereof include aromatic sulfonic acids and aliphatic sulfonic acids, such as p-toluenesulfonic acid and naphthalenesulfonic acid. In the case of the multilayered structure, such a compound may be added to any one of the layers.

The amount of the added compound is preferably from 0.05 to 5%, and more preferably from 0.1 to 3% by mass of all solid contents in the image recording layer. If this amount is too large, the solubilities of the respective layers in developing solution increase unfavorably.

Various dissolution adjusters may be added to the image recording layer of the invention to adjust the solubility. Preferable examples of the dissolution adjusters include disulfone compounds and sulfone compounds as described in JP-A No. 11-119418, a specific example of which is 4,4-bishydroxyphenylsulfone. In the case of the multilayered structure, such a compound may be added to any one of the layers.

The amount of the added compound is preferably from 0.05 to 20%, and more preferably from 0.5 to 10% by mass of all solid contents in the image recording layer.

In order to make the sensitivity higher, a cyclic acid anhydride, a phenol compound, or an organic acid may be used together. Examples of the cyclic acid anhydride include phthalic anhydride, tetrahydrophthalic anhydride, hexahydrophthalic anhydride, 3,6-endooxy-$\Delta$4-tetrahydrophthalic anhydride, tetrachlorophthalic anhydride, maleic anhydride, chloromaleic anhydride, $\alpha$-phenylmeleic anhydride, succinic anhydride, and pyromellitic anhydride which are described in U.S. Pat. No. 4,115,128. Examples of the phenol compound include bisphenol A, p-nitrophenol, p-ethoxyphenol, 2,4,4'-trihydroxybenzophenone, 2,3,4-trihydroxybenzophenone, 4-hydroxybenzophenone, 4,4',4"-trihydroxytriphenylmethane, and 4,4',3",4"-tetrahydroxy-3,5,3',5'-tetramethyltriphenylmethane. Examples of the organic acid include sulfonic acids, sulfinic acids, alkylsulfuric acid, phosphoric acids, phosphates, and carboxylates described in JP-A Nos. 60-88942 and 2-96755. Specific examples thereof include p-toluenesulfonic acid, dodecylbenzenesulfonic acid, p-toluenesulfinic acid, ethylsulfuric acid, phenylphosphonic acid, phenylphosphinic acid, phenyl phosphate, diphenyl phosphate, benzoic acid, isophthalic acid, adipic acid, p-toluic acid, 3,4-dimethoxybenzoic acid, phthalic acid, terephthalic acid, 4-cyclohexene-1,2-dicarboxylic acid, erucic acid, lauric acid, n-undecanoic acid, and ascorbic acid. The percentage of the cyclic acid anhydride, the phenol compound or the organic acid in the materials for the image recording layer is preferably from 0.05 to 20%, more preferably from 0.1 to 15%, and still more preferably from 0.1 to 10% by mass.

The following can be added to the image recording layer coating solution of the invention in order to heighten the stability of developing processing under wider developing conditions: nonionic surfactants described in JP-A Nos. 62-251740 and 3-208514, amphoteric surfactants described in JP-A Nos. 59-121044 and 4-13149, siloxane compounds described in EP No. 950517, and copolymers made from a fluorine-containing monomer, described in JP-A No. 11-288093.

In the case of the multilayered structure, such a compound may be added to either one of the upper and lower layers, or to both layers.

Specific examples of the nonionic surfactant include sorbitan tristearate, sorbitan monopalmitate, sorbitan trioleate, monoglyceride stearate, and polyoxyethylene nonyl phenyl ether. Specific examples of the amphoteric surfactant include alkyldi(aminoethyl)glycine, alkylpolyaminoethylglycine hydrochloride, 2-alkyl-N-carboxyethyl-N-hydroxyethylimidazolinium betaine, and N-tetradecyl-N,N-betaine type surfactants (for example, "Amorgen K" (trade name) manufactured by Dai-ichi Kogyo Seiyaku Co., Ltd.).

The siloxane compound is preferably block copolymer of dimethylsiloxane and polyalkylene oxide. Specific examples thereof include silicones modified with polyalkylene oxide, such as DBE-224, DBE-621, DBE-712, DBP-732 and DBP-534 (trade names) manufactured by Chisso Corp., and Tego Glide 100 (trade name) manufactured by Tego Co. of Germany.

The percentage of the nonionic surfactant and the amphoteric surfactant in the image recording layer coating solution is preferably from 0.05 to 15%, and more preferably from 0.1 to 5% by mass.

A printing-out agent for yielding a visible image immediately after the recording layer in the invention is heated by exposure to light can be added to the recording layer.

Typical examples of the printing-out agent are combinations of a compound which releases an acid caused by heat from exposure to light (photo acid-releaser) with an organic dye which can make a salt. Specific examples thereof include combinations of o-naphthoquinonediazide-4-sulfonic acid halogenide and a salt-forming organic dye, which are described in JP-A Nos. 50-36209 and 53-8128; and combinations of a trihalomethyl compound with a salt-forming organic dye, which are described in JP-A Nos. 53-36223, 54-74728, 60-3626, 61-143748, 61-151644 and 63-58440. As this trihalomethyl compound, an oxazole type compound or a triazine type compound are known. Both of them have excellent stability with the passage of time, and can provide a vivid printed-out image.

In the case of the multilayered structure, such a compound may be added to either one of the upper and lower layers, or to both layers. The amount of the added compound is preferably from 0.01 to 10%, and more preferably from 1 to 3% by mass of the image recording layer coating solution.

If necessary, a plasticizer to provide softness of the coating and so on may be added into the image recording layer of the invention. Examples thereof include butyl phthalate, polyethylene glycol, tributyl citrate, diethyl phthalate, dibutyl phthalate, dihexyl phthalate, dioctyl phthalate, tricresyl phosphate, tributyl phosphate, trioctyl phosphate, tetrahydrofurfuryl oleate, and oligomers or polymer of acrylic acid or methacrylic acid.

The planographic printing plate precursor to which the method of the invention can be applied can be produced by dissolving, into a solvent, components for the image recording layer coating solution and components for a coating solution for forming a desired layer such as a protective layer, and then applying the coating solutions on an appropriate support. In the case that the image recording layer has the multilayered structure, it is permissible to select whether or not each of the optional components is added into the upper layer or the lower layer, or to adjust the amounts of the components to be added, for example, in order to make the solubility of the lower layer higher than that of the upper layer.

The image recording layer having the multilayered structure can be formed by dissolving the above-mentioned respective components which constitute each of the upper and the lower layers into a solvent, and then applying the resultant solutions successively to a support.

In accordance with the purpose, a protective layer, a resin intermediate layer, a back coat layer or the like can be formed in the same way to form the image recording layer.

Examples of the solvent used in this step include ethylene dichloride, cyclohexanone, methyl ethyl ketone, methanol, ethanol, propanol, ethylene glycol monomethyl ether, 1-methoxy-2-propanol, 2-methoxyethylacetate, 1-methoxy-2-propylacetate, dimethoxyethane, methyl lactate, ethyl lactate, N,N-dimethylacetoamide, N,N-dimethylformamide, tetramethylurea, N-methylpyrrolidone, dimethylsulfoxide, sulfolane, y-butyrolactone, and toluene. However, the solvent is not limited to these examples. These solvents may be used alone or in a mixture form.

When the upper and the lower layers of the multilayered structure image recording layer are successively applied, from the viewpoint of suppressing the compatibility or mixture of the two layers in the interface therebetween to make the multilayered structure clear, it is preferable that the coating solvent for the upper layer is selected from solvents which do not dissolve the components constituting the lower layer (in particular, the alkali-soluble resin contained in the lower layer).

The concentration of the above-mentioned components (all solid contents containing the additives) in the solvent is preferably from 1 to 50% by mass.

The amount (of solid contents) of the coating obtained on the support after the application and drying varies depending on the purpose of the coating. In the case that the coating is the recording layer of the planographic printing plate precursor, in general the amount is preferably from 0.5 to 5.0 $g/m^2$.

In the case that the image recording layer has the multi-layered structure, the amount of the applied upper layer and that of the applied lower layer are appropriately adjusted depending on the purpose of the layer structure. In general, the amount of the applied upper layer is preferably approximately 0.05 to 1.0 $g/m^2$, and that of the applied lower layer is preferably approximately 0.3 to 3.0 $g/m^2$. The amount of the applied two layers is preferably from 0.5 to 3.0 $g/m^2$.

In both the monolayered structure and the multilayered structure, as the amount of the applied layer(s) falls, the apparent sensitivity of the recording layer increases but the film property thereof is reduced.

Various methods can be used for applying the layer(s). Examples thereof include bar coating, spin coating, spray coating, curtain coating, dip coating, air knife coating, blade coating and roll coating.

It is possible to add, to the recording layer coating solution in the invention, a surfactant to improve the coating property of the solution. An example of the surfactant is a fluorine-containing surfactant as described in JP-A No. 62-170950. The amount of the surfactant added is preferably from 0.01 to 1%, and more preferably from 0.05 to 0.5% by mass of all solid contents in the recording layer.

[Resin Intermediate Layer]

If necessary, a resin intermediate layer can be formed between the image recording layer and the support in the planographic printing plate precursor of the invention.

An advantage of forming this resin intermediate layer is that high sensitivity can be obtained for the following reasons: the recording layer, which is an infrared ray sensitive layer the solubility of which in alkali developing solution is improved by exposure to light, is formed so as to have a surface to be exposed or to be positioned near a surface to be exposed, whereby the recording layer has good sensitivity to an infrared ray laser; further, the resin intermediate layer, which is made of polymer, is disposed between the support and the infrared ray sensitive layer to function as a heat-insulating layer, so that heat generated by exposure to the infrared ray laser does not diffuse into the support so as to be effectively used to form an image. Moreover, this resin intermediate layer appears to be useful for the following reasons. That is, in the non-exposed portion, the recording layer itself, through which alkali developing solution does not permeate, functions as a protective layer for the resin intermediate layer so that the stability of this portion during development improves, an image excellent in discrimination is formed, and further the stability of this portion over time can be maintained. On the other hand, in the exposed portion, the components having cancelled dissolution-suppressing capability, in the recording layer, are rapidly dissolved or dispersed in developing solution and further this resin intermediate layer itself, which is disposed adjacent to the support, is made of alkali-soluble polymer; therefore, the intermediate layer has good solubility in developing solution. For example, even when a developing solution having low activity is used, the layer rapidly dissolves without any remains so that the developability of the recording layer improves.

A known ordinary method may be used for drying the respective layers. Examples of the method include the convection drying method, which is a method of applying, for example, the image recording layer, and then blowing hot air against the layer to dry the layer; the radiative heating method, which is a method of drying the layers by radiative heat from heating plates arranged over and below the support, as described in JP-A No. 60-149871; and the heat transfer heating method, which is a method of conducting a heat medium inside a roller and bringing the support into contact with this roller to dry the layers by heat transferred from the surface of the roller, as described in JP-A Nos. 60-21334 and-60-62778. The convection drying method is particularly preferable.

As for the developability of the planographic printing plate precursor, the electric conductivity of developing solution capable of forming an image is high (the developability is low) when the conditions for the drying are severe, whereas the electric conductivity of the developing solution capable of forming an image is low (the developability is high) when the conditions for the drying are mild. The drying conditions can be controlled by adjusting, for example, the temperature of the hot air, the blast volume thereof, the direction of the blast, the temperature of the heating plates, the material of the heating plates, the temperature of the heat medium which is conducted inside the rollers, the material of the heat medium, and other factors, correspondingly to each of the drying methods.

The amount of the solvent remaining in the image recording layer after the drying is preferably as little as possible. Specifically, the amount is preferably 80 $g/m^2$ or less, and more preferably 60 $g/m^2$ or less.

[Support]

The thin film to which the invention can be applied may be a thin film formed on a support. The type of this support is not particularly limited. The following describes, as an example, the support used in the planographic printing plate precursor. The support is a plate-form product which is dimensionally stable. Examples thereof include paper, paper laminated with a plastic (such as polyethylene, polypropylene, or polystyrene), metal plates (such as aluminum, zinc, copper plates), plastic films (such as cellulose diacetate, cellulose triacetate, cellulose propionate, cellulose lactate, cellulose acetate lactate, cellulose nitrate, polyethylene terephthalate, polyethylene, polystyrene, polypropylene, polycarbonate, and polyvinyl acetal films), and paper or plastic films laminated or vapor-deposited with a metal as described above.

The support of the invention is preferably a polyester film or an aluminum plate. An aluminum plate is particularly preferable since the plate has good dimensional stability and is relatively inexpensive. Preferable examples of the aluminum plate include a pure aluminum plate, and alloy plates comprising aluminum as the main component and a small amount of different elements. A plastic film laminated or vapor-deposited with aluminum may be used. Examples of the different elements contained in the aluminum alloy include silicon, iron, manganese, copper, magnesium, chromium, zinc, bismuth, nickel, and titanium. The content of the different elements in the alloy is at most 10% by mass. In the invention, pure aluminum is particularly preferable. However, since pure aluminum is not easily produced from the viewpoint of metallurgy technology, aluminum containing a minimal amount of different elements is also acceptable.

The aluminum plate used in the invention is not necessarily an aluminum plate having a specified composition, but may be any aluminum plate which has been known or used hitherto. The thickness of the aluminum plate used in the invention is generally from 0.1 to 0.6 mm, preferably from 0.15 to 0.4 mm, and more preferably from 0.2 to 0.3 mm.

Before the surface of the aluminum plate is roughened, the plate is subjected to degreasing treatment with a surfactant, an organic solvent, an aqueous alkali solution or the like if desired, in order to remove rolling oil on the surface. The roughening treatment of the aluminum surface is performed by various methods, for example, by a mechanically surface-roughening method, a method of dissolving and roughening the surface electrochemically, or a method of dissolving the surface selectively in a chemical manner. The mechanically surface-roughening method which can be used may be a known method, such as a ball polishing method, brush polishing method, a blast polishing method or a buff polishing method. The electrochemically surface-roughening method may be a method of performing surface-roughening in a hydrochloric acid or nitric acid electrolyte by alternating current or direct current. As disclosed in JP-A No. 54-63902, a combination of the two may be used. The aluminum plate, the surface of which is roughened as described above, is subjected to alkali-etching treatment and neutralizing treatment if necessary. Thereafter, the aluminum plate is subjected to anodizing treatment if desired, in order to improve the water holding ability or wear resistance of the surface. The electrolyte used in the anodizing treatment of the aluminum plate is any one selected from various electrolytes which can make a porous oxide film. Sulfuric acid, phosphoric acid, oxalic acid, chromic acid, or a mixed acid thereof are generally used. The concentration of the electrolyte may be appropriately decided depending on the type of the electrolyte.

Treatment conditions for the anodization cannot be specified since the conditions vary depending on the electrolyte used. However, the following conditions are generally suitable: an electrolyte concentration of 1 to 80% by mass, a solution temperature of 5 to 70° C., a current density of 5 to 60 A/dm$^2$, a voltage of 1 to 100 V, and an electrolyzing time of 10 seconds to 5 minutes. If the amount of the anodic oxide film is less than 1.0 g/m$^2$, the printing resistance is insufficient or non-image portions of the planographic printing plate are easily injured so that so-called "injury stains", resulting from ink adhering to injured portions at the time of printing, are easily generated. If necessary, the aluminum surface is subjected to treatment for hydrophilicity after the anodizing treatment. The treatment for hydrophilicity which can be used in the invention may be an alkali metal silicate (for example, aqueous sodium silicate solution) method, as disclosed in U.S. Pat. Nos. 2,714,066, 3,181,461, 3,280,734, and 3,902,734. In this method, the support is subjected to immersing treatment or electrolyzing treatment with aqueous sodium silicate solution. Alternatively, there may be used a method of treating the support with potassium fluorozirconate disclosed in JP-B No. 36-22063 or polyvinyl phosphonic acid, as disclosed in U.S. Pat. Nos. 3,276,868, 4,153,461, and 4,689,272.

The planographic printing plate precursor to which the invention is applied is a product wherein a positive recording layer is formed on a support. If necessary, an undercoat layer may be formed therebetween.

As components for the undercoat layer, various organic compounds may be used. Examples thereof include carboxymethylcellulose, dextrin, gum arabic, phosphonic acids having an amino group such as 2-aminoethylphosphonic acid, organic phosphonic acids such as phenylphosphonic acid, naphthylphosphonic acid, alkylphosphonic acid, glycerophosphonic acid, methylenediphosphonic acid and ethylenediphosphonic acid, each of which may have a substituent, organic phosphoric acids such as phenylphosphoric acid, naphthylphosphoric acid, alkylphosphoric acid and glycerophosphoric acid, each of which may have a substituent, organic phosphinic acids such as phenylphosphinic acid, naphthylphosphinic acid, alkylphosphinic acid, and glycerophosphinic acid, each of which may have a substituent, amino acids such as glycine and β-alanine, and hydrochlorides of amines having a hydroxyl group, such as hydrochloride of triethanolamine. These may be used in a mixture form.

Such an organic undercoat layer can be formed by the following methods: a method of dissolving the above-mentioned organic compound into water, an organic solvent such as methanol, ethanol or methyl ethyl ketone, or a mixed solvent thereof to prepare a solution, applying the solution onto an aluminum plate, and drying the solution to form the undercoat layer; or a method of dissolving the above-mentioned organic compound into water, an organic solvent such as methanol, ethanol or methyl ethyl ketone, or a mixed solvent thereof to prepare a solution, dipping an aluminum plate into the solution to cause the plate to absorb the organic compound, washing the plate with water or the like, and then drying the plate to form the undercoat layer. In the former method, the solution of the organic compound having a concentration of 0.005 to 10% by mass can be applied by various methods. In the latter method, the concentration of the organic compound in the solution is from 0.01 to 20%, preferably from 0.05 to 5% by mass; the dipping temperature is from 20 to 90° C., preferably from 25 to 50° C.; and the dipping time is from 0.1 second to 20 minutes, preferably from 2 seconds to 1 minute. The pH of the solution used in this method can be adjusted to 1–12 with a basic material such as ammonia, triethylamine or potassium hydroxide, or an acidic material such as hydrochloric acid or phosphoric acid. A yellow dye can be added to the solution in order to improve the reproducibility of the tone of the image recording material.

The coating amount of the organic undercoat layer is suitably from 2 to 200 mg/m$^2$, and preferably from 5 to 100 mg/m$^2$. If the coating amount is less than 2 mg/m$^2$, sufficient printing resistance cannot be obtained. If the coating amount is more than 200 g/m$^2$, the same result is obtained.

The planographic printing plate precursors to which the method of the invention can be applied are generally forwarded, transported and stored in the form of products wherein the printing plate precursors between which jointed paper is inserted are stacked and packaged.

At the time of plate-making and printing, a group wherein the jointed paper and the plate precursor are overlapped with each other is held, transferred, and fitted and fixed onto a position where the plate-making is performed, typically using an autoloader. Thereafter, the jointed paper is taken away, and in this state the plate precursor is imagewise exposed to light and developed. However, the step for forming an image is not limited to such a step. In the case of direct plate-making, the position where the plate-making is performed is on a printer.

The light source used in the image-exposure to light is preferably a light source having an emission wavelength within the range from near infrared ray wavelengths to infrared ray wavelengths, and is more preferably a solid laser or a semiconductor laser. The emission wavelength is preferably from 760 to 1200 nm.

As a developing solution and replenisher for the planographic printing plate precursor to which the invention can be applied, an aqueous alkali solution, which has been known hitherto, can be used. The aqueous alkali solution can be classified as a so-called "silicate developing solution", which is an alkali agent containing alkali silicate and silicon dioxide which contains silicon dioxide alkali silicate, and "non-silicate developing solution", which comprises a nonreducing sugar and a base but does not contain silicon dioxide substantially. The word "substantially" means that it is permissible that inevitable impurities and a trace amount of silicon dioxide as a byproduct are present.

The pH of the developing solution is preferably from 9.0 to 14.0, and more preferably from 12.0 to 13.5.

Firstly, the "silicate developing solution" will be described. Examples of the alkali silicate include inorganic alkali salts such as sodium silicate, potassium silicate, sodium triphosphate, potassium triphosphate, ammonium triphosphate, sodium biphosphate, potassium biphosphate, ammonium biphosphate, sodium carbonate, potassium carbonate, ammonium carbonate, sodium hydrogencarbonate, potassium hydrogencarbonate, ammoniumhydrogencarbonate, sodiumborate, potassium borte, ammonium borate, sodium hydroxide, ammonium hydroxide, potassium hydroxide and lithium hydroxide; and organic alkali agents such as monomethylamine, dimethylamine, trimethylamine, monoethylamine, diethylamine, triethylamine, monoisopropylamine, diisopropylamine, triisopropylamine, n-butylamine, monoethanolamine, diethanolamine, triethanolamine, monoisopropanolamine, diisopropanolamine, ethyleneimine, ethylenediamine, and pyridine. These alkali agents may be used alone or in combination of two or more thereof.

The developability of the aqueous alkali solution can be easily adjusted by adjusting the blend ratio between silicon oxide $SiO_2$ and alkali oxide $M_2O$ wherein M represents an alkali metal or an ammonium group, these two oxides being components of the silicate, and the concentration of the silicate. It is effective to use, for example, alkali metal silicates as described in JP-A No. 54-62004 or JP-B No. 57-7427.

Among the above-mentioned aqueous alkali solutions, a solution wherein the blend ratio of silicon oxide $SiO_2$ to alkali oxide $M_2O$ (the mole ratio of $SiO_2/M_2O$) is from 0.5 to 3.0 is preferable, and a solution wherein the mole ratio of $SiO_2/M_2O$ is 1.0 to 2.0 is more preferable.

If the mole ratio of $SiO_2/M_2O$ is less than 0.5, the alkali strength becomes strong to cause an adverse effect that an aluminum plate or the like, which is widely used as the support of the planographic printing plate precursor, is etched. If the mole ratio is more than 3.0, the developability thereof may fall.

The concentration of alkali silicate in the developing solution is preferably from 1 to 10%, more preferably from 3 to 8%, and most preferably from 4 to 7% by mass of the aqueous alkali solution.

If the concentration is less than 1% by mass, developability and processing ability may fall. If the concentration is more than 10% by mass, precipitation or crystallization easily occurs, and further at the time of neutralizing the developing solution for treating waste liquid thereof, the solution easily gelatinizes so that the treatment may be hindered.

Next, the "non-silicate developing solution" will be described. This developing solution comprises a nonreducing sugar and a base, as described above. The nonreducing sugar is a sugar having no reducing ability since the sugar has neither a free aldehyde group nor a ketone group, and is classified into a trehalose type oligosaccharide wherein reducing groups are bonded to each other, a glucoside wherein a reducing group of a sugar is bonded to a nonsugar, and a sugar alcohol obtained by reducing a sugar by hydrogenation. In the invention, any one of these sugars may be suitably used.

Examples of the trehalose type oligosaccharide include saccharose and trehalose. Examples of the glucoside include alkylglucosides, phenolglucosides, and mustard seed oil glucoside.

Examples of the sugar alcohol include D and L-arabite, ribitol, xylitol, D- and L-sorbitos, D- and L-adonite, D- and L-iditol, D- and L-talitol, D- and L-dulcitol, and D- and L-allodulcitol.

Preferable examples thereof include maltitol, obtained by hydrogenating a disaccharide, and a reductant obtained hydrogenating an oligosaccharide (i.e., reduced starch syrup).

Among the above-mentioned examples, sugar alcohol and saccharose are preferable as the nonreducing sugar. In particular, D-sorbitol, saccharose, and reduced starch syrup are more preferable since they have a buffer effect within an appropriate pH range.

These nonreducing sugars may be used alone or in combination of two or more thereof. The percentage thereof in the developing solution is preferably from 0.1 to 30%, and more preferably from 1 to 20% by mass.

The alkali silicate or the nonreducing sugar may be combined with an alkali agent, as a base, which is appropriately selected from known alkali agents.

Examples of the alkali agent include inorganic alkali agents (such as sodium hydroxide, potassium hydroxide, lithium hydroxide, trisodium phosphate, tripotassium phosphate, triammonium phosphate, disodium phosphate, dipotassium phosphate, diammonium phosphate, sodium carbonate, potassium carbonate, ammonium carbonate, sodium hydrogencarbonate, potassium hydrogencarbonate, ammonium hydrogencarbonate, sodiumborate, potassium borate and ammonium borate), potassium citrate, tripotassium citrate, sodium citrate, and organic alkali agents (such as monomethylamine, dimethylamine, trimethylamine, monoethylamine, diethylamine, triethylamine, monoisopropylamine, diisopropylamine, triisopropylamine, n-butylamine, monoethanolamine, diethanolamine, triethanolamine, monoisopropanolamine, diisopropanolamine, ethyleneimine, ethylenediamine, and pyridine).

These alkali agents may be used alone or in combination of two or more thereof.

Among the above-mentioned examples, sodium hydroxide or potassium hydroxide are preferable since the pH thereof can be adjusted within a wide range by adjusting the amount of the hydroxide added to the reducing sugar.

The non-silicate developing solution may be used together with an alkali buffer solution comprising a weak acid other than the above-mentioned nonreducing sugars, and a strong base. The weak acid preferably has a dissociation constant (pKa) of 10.0 to 13.2, and can be selected from weak acids described in "Ionization Constants of Organic Acids in Aqueous Solution" published by Pergam Press Co., and other documents.

Specifically, preferable examples thereof include alcohols such as 2,2,3,3-terafluoropropanol-1 (pKa: 12.74), trifluoroethanol (pKa: 12.37), and trichloroethanol (pKa: 12.24);

aldehydes such as pyridine-2-aldehyde (pKa: 12.68), and pyridine-4-aldehyde (pKa: 12.05);

compounds having a phenolic hydroxyl group, such as salicylic acid (pKa: 13.0), 3-hydroxy-2-naphthoic acid (pKa: 12.84), catechol (pKa: 12.6), gallic acid (pKa: 12.4), sulfosalicyclic acid (pKa: 11.7), 3,4-dihydroxysulfonic acid (pKa: 12.2), 3,4-dihydroxybenzoic acid (pKa: 11.94), 1,2, 4-trihydroxybenzene (pKa: 11.82), hydroquinone (pKa: 11.56), pyrogallol (pKa: 11.34), o-cresol (pKa: 10.33), resorcinol (pKa: 11.27), p-cresol (pKa: 10.27), andm-cresol (pKa: 10.09);

oximes such as 2-butanoneoxime (pKa: 12.45), acetoxime (pKa: 12.42), 1,2-cycloheptanedionedioxime (pKa: 12.3), 2-hydroxybenzaldehydeoxime (pKa: 12.10), dimethylglyoxime (pKa: 11.9), ethanediamidedioxime (pKa: 11.37), and acetophenoneoxime (pKa: 11.35);

nucleic acid related materials such as adenosine (pKa: 12.56), inosine (pKa: 12.5), guanine (pKa: 12.3), cytosine (pKa: 12.2), hypoxanthine (pKa: 12.1), and xanthine (pKa: 11.9); and other materials, such as diethylaminomethylphosphonic acid (pKa: 12.32), 1-amino-3,3,3-trifluorobenzoic acid (pKa: 12.29), isopropylidenediphosphonic acid (pKa: 12.10), 1,1-ethylidenediphosphonic acid (pKa: 11.54), 1,1-ethylidenediphosphonic acid 1-hydroxy (pKa: 11.52), benzimidazole (pKa: 12.86), thiobenzamide (pKa: 12.8), picolinethioamide (pKa: 12.55), and barbituric acid (12.5).

Among these weak acids, sulfosalicylic acid and salicylic acid are preferable.

Preferable examples of the strong base combined with these weak acids include sodium hydroxide, ammonium hydroxide, potassium hydroxide, and lithium hydroxide.

These strong bases may be used alone or in combination of two or more thereof. The strong base is used in a state in which the pH thereof is adjusted within a preferable range by appropriately selecting the concentration thereof and in combination with the weak acid.

If necessary, the following may be added, as other components, to the alkali developing solution and replenisher in order to promote the developability thereof, disperse development scum, and improve the ink-affinity of the image portion of the planographic printing plate precursor: a development stabilizer, organic solvent, reducing agent, organic carboxylic acid, hard water softener, surfactant, known preservative, colorant, thickener and antifoaming agent, and other known agents.

Preferable examples of the surfactant include anionic, cationic, nonionic and amphoteric surfactants. If necessary, the following may be added to the alkali developing solution and replenisher: a reducing agent (such as hydroquinone, resorcin, a sodium salt or a potassium salt of an inorganic acid such as sulfurous acid or sulfurous hydroacid), an organic carboxylic acid, an antifoaming agent or a hard water softener.

The printing plate precursor developed with the above-mentioned alkali developing solution and replenisher is post-treated with washing water, a rinse solution containing a surfactant or the like, or desensitizing liquid containing gum arabic or a starch derivative. As post-treatment of the printing plate precursor, these treatments may be used in combination thereof.

In recent years, an auto developing machine for developing printing plates has become widely used in order to rationalize and standardize plate-making work in the plate-making and printing industries. This automatic developing machine is generally composed of a developing section and a post-treating section, and comprises a device for carrying printing plates, various treating solution tanks, and spray devices. This machine pumps and a prays respective treating solutions onto an exposed printing plate from spray nozzles while carrying the printing plate horizontally. Also known recently, is a method of immersing and carrying a printing plate in tanks filled with treating solutions by means of in-liquid guide rolls. Such an automatic processing can be performed while replenishers are replenished into the respective treating solutions in accordance with the amounts to be treated, working time, and other factors. A so-called use-and-dispose processing method is also used, in which respective treatments are conducted with virtually unused treating solutions.

The planographic printing plate precursor to which the invention can be applied is imagewise exposed to light, developed, and subjected to water washing and/or rinsing and/or desensitizing. In the case that the resultant planographic printing plate has an unnecessary image portion (for example, a film edge trace of an original image film), the unnecessary image portion is removed. Preferably, such removal is performed by applying an erasing solution to the unnecessary image portion as described in JP-B No. 2-13293, allowing the resultant to stand as it is for several hours, and then washing the printing plate with water. It is also permissible to use a method of radiating active light rays introduced through an optical fiber onto the unnecessary image portions, as described in JP-A No. 59-174842, and then developing the resultant.

The planographic printing plate obtained as described above is coated with a desensitizing gum if desired, and subsequently the plate is subjected to a printing step. In order to enhance the printing resistance of the planographic printing plate, the plate is subjected to burning treatment. when the planographic printing plate is subjected to burning treatment, the plate is preferably treated with a surface-adjusting solution (i.e., smoothing liquid) before the burning as described in JP-B Nos. 61-2518 and 55-28062, and JP-A Nos. 62-31859 and 61-159655.

The method for the treatment is, for example, a method of applying the surface-adjusting solution onto the planographic printing plate with a sponge or absorber cotton infiltrated with this solution, a method of immersing the planographic printing plate in a vat filled with the surface-adjusting solution, or a method of applying the surface-adjusting solution to the planographic printing plate with an automatic coater. If the amount of the applied solution is made even with a squeegee or a squeegee roller after the application thereof, a more preferable result is provided.

In general, the amount of the applied surface-adjusting solution is suitably from 0.03 to 0.8 $g/m^2$ (dry mass). The planographic printing plate onto which the surface-adjusting solution is applied is dried if necessary, and then the plate is heated to high temperature by a burning processor. (for example, a burning processor (BP-1300) sold by Fuji Photo Film Co., Ltd.) or the like. The heating temperature and the heating time in this case, which depend on the types of the components which form the image, are preferably from 180 to 300° C. and from 1 to 20 minutes, respectively.

If necessary, the planographic printing plate subjected to the burning treatment can be subjected to treatments which have been conventionally conducted, such as water-washing treatment and gum coating treatment. However, in the case of using the surface-adjusting solution which contains a water soluble polymer compound or the like, the so-called desensitizing treatment (for example, the gum coating) can be omitted. The planographic printing plate obtained by treatments as described above is set to an offset printing machine or some other printing machine, and is used for printing images on a great number of sheets.

The above has described the planographic printing plate precursor to which the thin film analyzing method of the invention can be preferably applied. The method of the invention can be applied to not only such a thin film, which is formed on a support by a coating, but also to any thin film that is laminated on a support and can be cut with a cutting edge made of glass, a typical example of which is a microtome. The invention has an advantage in that the distribution state of an effective component in such a thin film along the depth direction thereof, and other properties can be correctly analyzed. The analyzing method of the invention having such a characteristic can be applied in order to analyze, for example, micro photoresist coatings for semiconductors, photosensitive insulating films, dry film resist films, various anti-reflecting films, wide view films for liquid crystal displays, color filters for liquid crystal displays, protective layers for liquid crystal displays, oriented films for liquid crystal displays, phase difference films for liquid crystal displays, light-polarizing films for liquid crystal displays, anti-reflecting films for liquid crystal displays, luminance improving films for liquid crystal displays, prism sheets for liquid crystal displays, diffusing films for liquid crystal displays, reflecting films for liquid crystal displays, various laminating films for organic EL, plastic optical fibers, color filters for image sensors, interlayer dielectrics, films for holography, various painting films (coatings) for automobiles, and other films.

EXAMPLES

The present invention is described byway of the following examples. However, the invention is not limited to these examples.

[Production of a Substrate]

An aluminum plate (raw material: 1050) having a thickness of 0.3 mm was washed with trichloroethylene, so as to be degreased. Thereafter, the surface thereof was roughened with a nylon brush and a suspension of 400-mesh pumice in water, and sufficiently washed with water. This plate was immersed into a 25% solution of sodium hydroxide in water at 45° C. for 9 seconds, so as to be etched. The plate was washed with water, immersed into 20% nitric acid for 20 seconds, and washed with water. The etched amount of the roughened surface was about 3 g/m² at this time. Next, this plate was anodized, using 7% sulfuric acid as an electrolyte, at a current density of 15 A/dm² to form a 3 g/m² direct-current anodic oxide film. Thereafter, the plate was washed with water, and dried. Furthermore, the plate was treated with a 2.5% by mass solution of sodium silicate in water at 30° C. for 10 seconds, and the following undercoating solution was applied onto the plate. The coating was dried at 80° C. for 15 seconds to yield a substrate (support). The application quantity of the coating after the drying was 15 mg/m².

[Undercoating Solution]

| The following polymer compound | 0.3 g |
|---|---|
| Methanol | 100 g |
| Water | 1 g |
| Molecular weight: 28000 | |

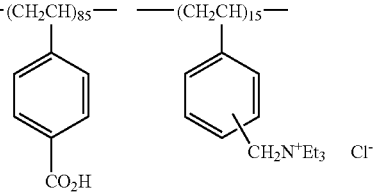

Molecular weight: 28000

(Formation of a Planographic Printing Plate Precursor 1)

An image recording layer having the following formulation was formed on the substrate as described above, so as to yield a planographic printing plate precursor 1.

(Image Recording Layer 1)

A lower layer coating solution 1 having the following composition was applied onto the substrate with a wire bar giving a wet application quantity of 19 ml/m², and then dried. Next, an image recording layer (upper layer) coating solution 1 having the following composition was applied onto the lower layer with a wire bar giving a wet application quantity of 19 ml/m², and then dried to yield a planographic printing plate precursor 1.

(Lower Layer Coating Solution 1)

| Binder N-(4-amino sulfonylphenyl)methacrylamide/acrylonitrile/methyl methacrylate (36/34/30, weight average molecular weight: 5000) | 2.133 g |
|---|---|
| Cyanine dye A (having the following structure) | 0.109 g |
| 4,4-Bishydroxyphenylsulfone | 0.126 g |
| Tetrahydrophthalic anhydride | 0.190 g |
| p-Toluenesulfonic acid | 0.008 g |
| Dye wherein the counter anion in Ethyl Violet was changed to 6-hydroxynaphthalenesulfonic acid | 0.100 g |
| 3-Methoxy-4-diazophenylaminehexafluorophosphate (thermally-decomposing compound) | 0.03 g |
| Fluorine-containing surfactant (MEGAFACE F176, manufactured by Dainippon Ink & Chemicals, Inc.) | 0.035 g |
| Methyl ethyl ketone | 26.6 g |
| 1-Methoxy-2-propanol | 13.6 g |
| γ-Butyrolactone | 13.8 g |
| Cyanine dye A | |

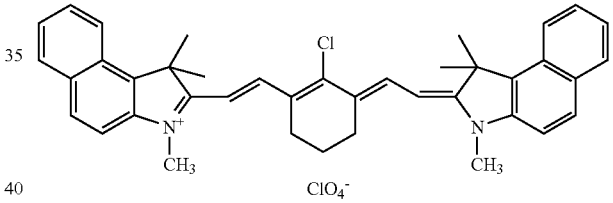

(Image Recording Layer Coating Solution 1)

| m,p-Cresol novolak (PR 54046, manufactured by Sumitomo Durez Co.) | 0.348 g |
|---|---|
| Cyanine dye A (having the above-illustrated structure) | 0.0192 g |
| Tetraethylammonium bromide | 0.030 g |
| Fluorine-containing surfactant (MEGAFACE F176, manufactured by Dainippon Ink & Chemicals, Inc.) | 0.035 g |
| Methyl ethyl ketone | 26.6 g |
| 1-Methoxy-2-propanol | 13.6 g |

(Formation of a Planographic Printing Plate Precursor 2)

An image recording layer having the following formulation was formed on the substrate as described above, so as to yield a planographic printing plate precursor 2.

(Image Recording Layer 2)

A lower layer coating solution 2 having the following composition was applied onto the substrate with a wire bar giving a wet application quantity of 19 ml/M², and then dried. Next, an image recording layer (upper layer) coating solution 2 having the following composition was applied onto the lower layer with a wire bar giving a wet application quantity of 19 ml/m², and then dried to yield a planographic printing plate precursor 2.

(Lower Layer Coating Solution 2)

| | |
|---|---|
| Binder N-phenylmaleimide/methacrylamide/methacrylic acid (45/40/15, average molecular weight: 5000) | 4.8 g |
| Dye wherein the counter ion in cyanine dye A (having the above-illustrated structure) was changed to p-toluenesulfonic acid | 0.2 g |
| Methyl acetate/methanol/dioxane (15:42.5:42.5) | 45 g |

(Image Recording Layer Coating Solution 2)

| | |
|---|---|
| m,p-Cresol novolak (PR 54046, manufactured by Sumitomo Durez Co.) | 4.85 g |
| Dye wherein the counter anion in Ethyl Violet was changed to 6-hydroxynaphthalenesulfonic acid | 0.15 g |
| Methyl ethyl ketone | 26.6 g |
| 1-Methoxy-2-propanol | 13.6 g |

[Formation of Comparative Example 1]

An image recording layer 3 having the following formulation was formed on the substrate as described above, so as to yield a planographic printing plate of Comparative Example 1.

(Comparative Image Recording Layer)

An image recording layer coating solution 3 having the following composition was applied onto the substrate with a wire bar giving a wet application quantity of 19 ml/m², and then dried to yield a planographic printing plate precursor of Comparative Example 1.

(Image Recording Layer Coating Solution 3)

| | |
|---|---|
| N-(4-aminosulfonylphenyl)methacrylamide/acrylonitrile/methyl methacrylate (35/30/35, weight average molecular weight: 50000) | 2.370 g |
| m,p-Cresol novolak (PR 54046, manufactured by Sumitomo Durez Co.) | 0.474 g |
| Cyanine dye A (having the above-illustrated structure) | 0.109 g |
| 4,4-Bis(hydroxyphenyl)sulfone | 0.126 g |
| Tetrahydrophthalic anhydride | 0.190 g |
| p-Toluenesulfonic acid | 0.008 g |
| Dye wherein the counter anion in Ethyl Violet was changed to 6-hydroxynaphthalenesulfonic acid | 0.100 g |
| Dimyristyl 3,3'-thiodipropionate | 0.030 g |
| Di-n-dodecyl 3,3'-thiodipropionate | 0.030 g |
| Fluorine-containing surfactant (MEGAFACE F-176, manufactured by Dainippon Ink & Chemicals, Inc.) | 0.035 g |
| Fluorine-containing surfactant (Defenser MCF-312, manufactured by Dainippon Ink & Chemicals, Inc.) | 0.035 g |
| Methyl ethyl ketone | 26.6 g |
| 1-Methoxy-2-propanol | 13.6 g |
| γ-Butyrolactone | 13.8 g |

Examples 1 to 3

1. Measurement for In-Layer Distributions of the Infrared Ray Absorber and the Colorant An obliquely-cutting edge (glass knife, edge angle: 45°) of the microtome described in the text of the present specification was used to cut each of the resultant planographic printing plate precursors at a cutting angle of 1° and a cutting speed of 0.5 mm/sec. Thereafter, the cut section was analyzed by TOF-SIMS analysis under the conditions described in the text of the specification, to evaluate the in-layer distributions of the infrared ray absorber and the colorant.

In the image recording layer of the planographic printing plate precursor 1, the infrared ray absorber was distributed in the upper portion and the colorant was distributed in the lower portion. The cos θ after smoothing was 0.75.

In the image recording layer of the planographic printing plate precursor 2, the colorant was distributed in the upper portion and the infrared ray absorber was distributed in the lower portion. The cos θ was 0.37.

In the image recording layer of the planographic printing plate precursor of Comparative Example 1, the distribution of the infrared ray absorber and that of the colorant overlapped with each other. The cos θ was 0.85.

[Evaluation of the Planographic Printing Plate Precursors]

For reference, the resultant planographic printing plate precursors were evaluated on the scratch resistance, the development latitude, the electric conductivity at which the image recording layer was decreased (development resistance) and the printing resistance thereof by methods described below. The results are shown in Table 1 described below.

The respective evaluating tests used a developing solution DT-1 manufactured by Fuji Photo Film Co., Ltd.

(Scratch Resistance)

Using a scratch tester manufactured by HEIDON Co., a load was applied to its sapphire (1.0 mm) to scratch each of the planographic printing plate precursors. Thereafter, the printing plate precursor was developed with developing solutions (the DT-1 diluted to have an electric conductivity of 45 mS/cm, and developing solution A diluted to have an electric conductivity of 75 mS/cm). The load at which a scratch was observed with the naked eye was displayed. The larger the numerical value, the better the scratch resistance.

(Evaluation of Development Latitude)

A machine (Trendsetter) manufactured by Creo Co. was used to print a test pattern imagewise on each of the resultant planographic printing plate precursors at an exposure energy of 90 mJ/cm².

Thereafter, each of the above-mentioned developing solutions was diluted to change the electric conductivity thereof, and the printing plate precursor was developed therewith. In this way, the electric conductivity at which the image recording layer in the exposed portion (non-image portion) was completely removed was measured. This was defined as the initial electric conductivity. At this time, the image density in the non-exposed portion (image portion) was measured with a GRETAG reflection densitometer D196 (manufactured by Gretag Macbeth Co.).

Next, the development was continued while the electric conductivity was changed. When an image portion having an image density smaller than the above-mentioned image density (the density of the image portion at the initial electric conductivity) by 0.06 or more (?) was formed, the electric conductivity of the developing solution was measured. The electric conductivity at this time (the electric conductivity just before undesired development was performed in the image portion, that is, the electric conductivity at which decrease in the image recording layer started) was defined as the maximum electric conductivity. The bigger the difference between the maximum electric conductivity and the initial electric conductivity, the wider the latitude within which the developing solutions can be used, that is, the development latitude is better. It can be said that the planographic printing plate precursor having a high maximum electric conductivity at this time has high development resistance of the image portion.

Numerical numbers shown as "Development latitude" in Table 1, for example, 37 to 55 means that the initial electric conductivity was 37 mS/cm and the maximum electric conductivity was 55 mS/cm.

TABLE 1

| | Distribution of the specific components (cosθ) | Scratch resistance | Development latitude |
|---|---|---|---|
| Planographic printing plate precursor 1 | 0.75 | 4 g | 37–55 |
| Planographic printing plate precursor 2 | 0.37 | 10 g | 37–57 |
| Planographic printing plate precursor of comparatire Example 1 | 0.85 | 2 g | 41–47 |

As is evident from Table 1, planographic printing plate precursors 1 and 2, in which the in-layer distribution of the infrared ray absorber and that of the colorant were different from each other, had excellent scratch resistance and development latitude. On the other hand, the planographic printing plate precursor of the Comparative Example had insufficient scratch resistance and development latitude. Among planographic printing plate precursors 1 and 2, precursor 2, wherein the cos θ obtained from TOF-SIMS analysis was small (the difference between the distribution states was large) and the infrared ray absorber was distributed in the lower portion, had particularly excellent scratch resistance and development latitude. From these results, according to the thin film analyzing method of the invention, the distribution states of specific components in a thin film (the infrared ray absorber and the colorant in the present examples) can be analyzed. Thus, the performance of an image recording layer can be determined.

What is claimed is:

1. A thin film analyzing method for analyzing a constituent of a thin film, which comprises a cutting step of cutting the thin film obliquely and an analyzing step of analyzing the cut section of the thin film,
   wherein the analyzing step is a step for measuring a distribution state of a specific component in the cut section of the thin film, and
   wherein the distribution state of the specific component is analyzed by TOF-SIMS in the analyzing step.

2. A thin film analyzing method according to claim 1, wherein the thin film is a thin film formed on a support.

3. A thin film analyzing method according to claim 1, wherein the thin film has a multilayered structure.

4. A thin film analyzing method according to claim 2, wherein the thin film is formed on a support and has a monolayered or multilayered structure.

5. A thin film analyzing method for analyzing a constituent of a thin film, which comprises a cutting step of cutting the thin film obliquely and an analyzing step of analyzing the cut section of the thin film,
   wherein the analyzing step is a step for measuring a distribution state of a specific component in the out section of the thin film, and
   wherein the distribution state of the specific component is analyzed by μ-ESCA in the analyzing step.

6. A thin film analyzing method according to claim 1, wherein the thin film is out with a microtome to which a cutting edge made of glass is fitted in the cutting step.

7. A thin film analyzing method according to claim 4, wherein the thin film is cut with a microtome to which a cutting edge made of glass is fitted in the cutting step.

8. A thin film analyzing method according to claim 6, wherein an edge angle of the cutting edge made of glass is 55° or less.

9. A thin film analyzing method according to claim 7, wherein an edge angle of the cutting edge made of glass is 55° or less.

10. A thin film analyzing method according to claim 1, wherein an angle for the cutting is set to 5° or less in the cutting step, thereby enlarging an area of the cut section in a film thickness direction 10 to 2800 times as compared with a case in which the thin film is cut perpendicularly to the surface of the thin film.

11. A thin film analyzing method according to claim 4, wherein an angle for the cutting is set to 5° or less in the cutting step, thereby enlarging an area of the cut section in a film thickness direction 10 to 2800 times as compared with a case in which the thin film is cut perpendicularly to the surface of the thin film.

12. A thin film analyzing method according to claim 1, wherein the thin film is a photosensitive thin film.

13. A thin film analyzing method according to claim 12, wherein the photosensitive thin film is an image recording layer comprising a water-insoluble and alkali-soluble resin, an infrared ray absorber, and a colorant.

14. A thin film analyzing method according to claim 1, wherein the thin film is a photosensitive thin film which is formed on a support and comprises a water-insoluble and alkali-soluble resin, an infrared ray absorber, and a colorant, and in the analyzing step the distributions of the infrared ray absorber and the colorant in the thin film are analyzed.

15. A thin film analyzing method according to claim 5, wherein the thin film is a thin film formed on a support.

16. A thin film analyzing method according to claim 5, wherein the thin film has a multilayered structure.

17. A thin film analyzing method according to claim 5, wherein the thin film is formed on a support and has a monolayered or multilayered structure.

18. A thin film analyzing method according to claim 5, wherein the thin film is cut with a microtome to which a cutting edge made of glass is fitted in the cutting step.

19. A thin film analyzing method according to claim 5, wherein the thin film is cut with a microtome to which a cutting edge made of glass is fitted in the cutting step.

20. A thin film analyzing method according to claim 18, wherein an edge angle of the cutting edge made of glass is 55° or less.

21. A thin film analyzing method according to claim 19, wherein an edge angle of the cutting edge made of glass is 55° or less.

22. A thin film analyzing method according to claim 5, wherein an angle for the cutting is set to 5° or less in the cutting step, thereby enlarging an area of the cut section in a film thickness direction 10 to 2800 times as compared with a case in which the thin film is cut perpendicularly to the surface of the thin film.

23. A thin film analyzing method according to claim 17, wherein an angle for the cutting is set to 5° or less in the cutting step, thereby enlarging an area of the cut section in a film thickness direction 10 to 2800 times as compared with a case in which the thin film is cut perpendicularly to the surface of the thin film.

24. A thin film analyzing method according to claim 5, wherein the thin film is a photosensitive thin film.

25. A thin film analyzing method according to claim 24, wherein the photosensitive thin film is an image recording layer comprising a water-insoluble and alkali-soluble resin, an infrared ray absorber, and a colorant.

26. A thin film analyzing method according to claim 5, wherein the thin film is a photosensitive thin film which is formed on a support and comprises a water-insoluble and alkali-soluble resin, an infrared ray absorber, and a colorant, and in the analyzing step the distributions of the infrared ray absorber and the colorant in the thin film arc analyzed.

* * * * *